(12) United States Patent
Kurn

(10) Patent No.: US 6,815,164 B2
(45) Date of Patent: Nov. 9, 2004

(54) METHODS AND PROBES FOR DETECTION AND/OR QUANTIFICATION OF NUCLEIC ACID SEQUENCES

(75) Inventor: Nurith Kurn, Palo Alto, CA (US)

(73) Assignee: NuGEN Technologies, Inc., San Carlos, CA (US)

( * ) Notice: Subject to any disclaimer, the term of this patent is extended or adjusted under 35 U.S.C. 154(b) by 8 days.

(21) Appl. No.: 09/974,756

(22) Filed: Oct. 9, 2001

(65) Prior Publication Data

US 2002/0115088 A1 Aug. 22, 2002

Related U.S. Application Data

(60) Provisional application No. 60/238,850, filed on Oct. 6, 2000.

(51) Int. Cl.[7] .......................... C12Q 1/68; C12P 19/34; C07H 21/02; C07H 21/04
(52) U.S. Cl. .................. 435/6; 435/91.1; 435/91.2; 536/23.1; 536/24.3
(58) Field of Search .................. 435/6, 91.1, 91.2; 536/23.1, 24.3

(56) References Cited

U.S. PATENT DOCUMENTS

| | | | |
|---|---|---|---|
| 3,996,345 | A | 12/1976 | Ullman et al. |
| 4,174,384 | A | 11/1979 | Ullman et al. |
| 4,261,968 | A | 4/1981 | Ullman et al. |
| 4,458,066 | A | 7/1984 | Caruthers et al. |

(List continued on next page.)

FOREIGN PATENT DOCUMENTS

| | | |
|---|---|---|
| CA | 2244964 | 4/1999 |
| EP | 0909823 A2 A3 | 4/1999 |
| JP | 11-155598 | 4/1999 |
| WO | WO 99/42615 | 8/1999 |
| WO | WO 99/42616 | 8/1999 |
| WO | WO 00/06778 | 2/2000 |
| WO | WO 00/15848 | 3/2000 |

OTHER PUBLICATIONS

Agrawal, S. and Zemecnik, P. (1990). "Site Specific Functionalization of Oligonucleotides for Attaching Two Different Reporter Groups," *Nucl. Acids Res.* 18(18):5419–5423.

Beaucage, S. L. et al. (1981), "Deoxynucleoside Phosphoramidites—A New Class of Key Intermediates for Deoxypolynucleotide Synthesis," *Tetrahedron Letter*, 22:1859–1862.

(List continued on next page.)

*Primary Examiner*—Jeffrey Fredman
*Assistant Examiner*—Teresa Strzelecka
(74) *Attorney, Agent, or Firm*—Morrison & Foerster LLP

(57) ABSTRACT

The present invention discloses nucleic acid detector probes for specific detection and/or quantification of target nucleic acid sequences and detection and/or quantification methods using these probes. In the absence of target nucleic acid sequence, a first oligonucleotide and a third oligonucleotide are bound to each other in a conformation which brings two member of an interacting moiety pair (labels) into close spatial proximity. Cooperative binding of the first oligonucleotide and a second oligonucleotide to a target nucleic acid sequence causes displacement of the third oligonucleotide from the first oligonucleotide probe resulting in separation of the two members of the interacting moiety pair (labels). The spatial separation of the moieties (labels) is detectable, and indicates the presence and/or amount of the target nucleic acid sequence. The method is useful for detection and/or quantification of a specific nucleic acid sequence as well as the detection of sequence alteration in the target nucleic acid sequence.

46 Claims, 13 Drawing Sheets

U.S. PATENT DOCUMENTS

| | | | |
|---|---|---|---|
| 4,582,788 A | 4/1986 | Erlich | |
| 4,683,202 A | 7/1987 | Mullis | |
| 4,876,187 A | 10/1989 | Duck et al. | |
| 4,996,143 A | 2/1991 | Heller et al. | |
| 5,169,766 A | 12/1992 | Schuster et al. | |
| 5,340,716 A | 8/1994 | Ullman et al. | |
| 5,399,491 A | 3/1995 | Kacian et al. | |
| 5,403,711 A | 4/1995 | Walder et al. | |
| 5,427,929 A | 6/1995 | Richards et al. | |
| 5,480,784 A | 1/1996 | Kacian et al. | |
| 5,491,063 A | 2/1996 | Fisher et al. | |
| 5,554,516 A | 9/1996 | Kacian et al. | |
| 5,554,517 A | 9/1996 | Davey et al. | |
| 5,565,322 A | 10/1996 | Heller | |
| 5,648,211 A | 7/1997 | Fraiser et al. | |
| 5,654,142 A | 8/1997 | Kievits et al. | |
| 5,679,512 A | 10/1997 | Laney et al. | |
| 5,683,879 A | 11/1997 | Laney et al. | |
| 5,688,648 A | 11/1997 | Mathies et al. | |
| 5,709,994 A | 1/1998 | Pease et al. | |
| 5,766,849 A | 6/1998 | McDonough et al. | |
| 5,824,517 A | 10/1998 | Cleuziat et al. | |
| 5,824,518 A | 10/1998 | Kacian et al. | |
| 5,876,976 A | 3/1999 | Richards et al. | |
| 5,888,779 A | 3/1999 | Kacian et al. | |
| 5,925,517 A | 7/1999 | Tyagi et al. | |
| 5,935,791 A | 8/1999 | Nadeau et al. | |
| 6,027,923 A | 2/2000 | Wallace | |
| 6,030,774 A | 2/2000 | Laney et al. | |
| 6,037,152 A | 3/2000 | Richards et al. | |
| 6,130,047 A | 10/2000 | Nadeau et al. | |
| 6,251,639 B1 | 6/2001 | Kurn | |
| 6,261,784 B1 | 7/2001 | Nadeau et al. | |
| 6,451,588 B1 * | 9/2002 | Egholm et al. | 435/287.2 |

OTHER PUBLICATIONS

Brown, E. L. et al. (1979). "Chemical Synthesis and Cloning of a Tyrosine tRNA Gene," *Methods in Enzymology,* 68:109–151.

Freier et al. (1986). "Improved Free–Energy Parameters for Predictions of RNA Duplex Stability", *Proc. Natl. Acad. Sci USA* 83:9373–9377.

Goodchild, J. (1990). "Conjugates of Oligonucleotides and Modified Oligonucleotides: A Review of Their Sytnesis and Properties," *Bioconjugate Chemistry,* 1(3):165–187.

MacMillan, A. M. and Vetdine, G. L. (1990). "Synthesis of Functionally Tethered Oligodeoxynucleotides by the Convertible Nucleotide Approach," *J. Org. Chem.,* 55:5931–5933.

Nadeau, J. G. et al. (1999). "Real–Time, Sequence–Specific Detection of Nucleic Acids During Strand Displacement Amplication," *Anal Biochem.* 276:177–187.

Narang, S. A et al. (1979),. "Improved Phosphostriester Method for the Synthesis of Gene Fragments," *Meth Enzymol.* 68:90–98.

Nurmi, J. et al. (2000). "A New Label Technology for the Detection of Specific Polymerase Chain Reaction Products in a Closed Tube," *Nucleic Acid Res.* 28(8):i–vi.

Patel, U. et al. (1996). "Formation of Chimeric DNA Primer Extension Products by Template Switching Onto an Annealed Downstream Oligonucleotide," *Proc. Nat'l. Acad. Sci USA* 93:2969–2974.

Pieles, U. et al. (1989). "Preparation of a Novel Psoralen Containing Deoxyadenosine Building Block for the Facile Solid Phase Synthesis of Psoralen–Modified Oligonucleotides for a Sequence Specific Crosslink to a Given Target Sequence," *Nucl. Acids. Res.* 17(22):8967–8978.

Rogert, A. et al. (1989). "Synthesis and Use of Labelled Nucleoside Phosphoramidite Building Blocks Bearing a Reporter Group: Biotinyl, Dinitrophenyl, Pyrenyl and Dansyl", *Nucleic Acids Research,* 17(19):7643–7651.

Tesler, J. et al. (1989). "Synthesis and Characterization of DNA Oligomers and Duplexes Containing Covalently Attached Molecular Labels: Comparison of Biotin, Fluorescein, and Pyrene Labels by Thermodynamic and Optical Spectroscopic Measurements," *J. Am. Chem. Soc.* 111:6966–6976.

Tinoco, I. et al. (1973). "Improved Estimation of Secondary Strucutre in Ribonucleic Acids," *Nature New Biology* 246:40–41.

Wu, D. Y. et al. (1989). "The Ligation Amplification Reaction (LAR)—Amplification of Specific DNA Sequences Using Sequential Rounds of Template–Dependent Ligation," *Genomics* 4:560–569.

* cited by examiner

Figure 1a: Probe A

Figure 1b: Probe B

Figure 1c: Probe C

Figure 6a
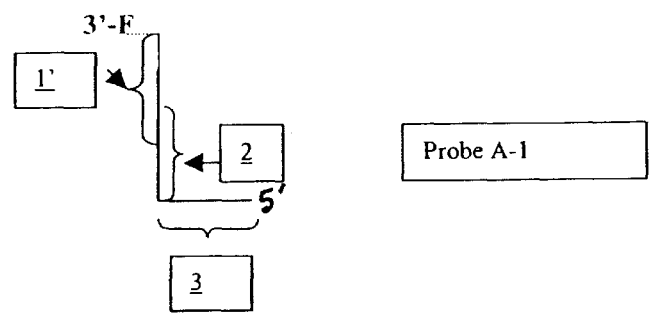
Figure 6b
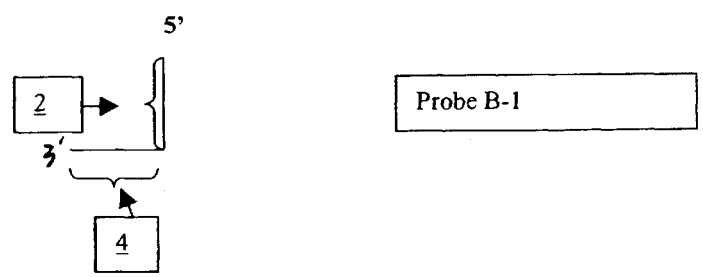
Figure 6c
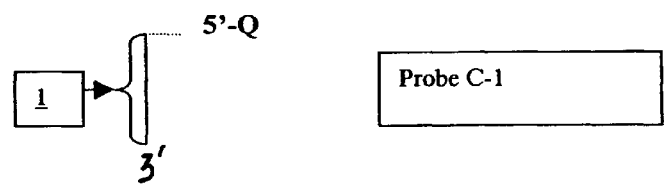
Figure 6

SEQUENCE LISTING

<160> NUMBER OF SEQ ID NOS: 4

<210> SEQ ID NO 1
<211> LENGTH: 217
<212> TYPE: DNA
<213> ORGANISM: Artificial Sequence
<220> FEATURE:
<223> OTHER INFORMATION: Synthetic Construct

<400> SEQUENCE: 1
agattcagtg aaggatagtg ctgaatttcc atctctgagt tcaaaataat ttgagaaaat    60
atgatagaaa ttgtgaagta ctagatttca gaaaatatga ttagaaaaag cgtggtacat   120
cttaaaatat aactttctgg cactgaatcc tgccacctac catctccacc tctaacatgg   180
atgcagttta taattaagag ctttcagatt ttgagca                            217

<210> SEQ ID NO 2
<211> LENGTH: 27
<212> TYPE: DNA
<213> ORGANISM: Artificial Sequence
<220> FEATURE:
<223> OTHER INFORMATION: Synthetic Construct

<400> SEQUENCE: 2
gtagtagtac attagcatta gcttctg                                        27

<210> SEQ ID NO 3
<211> LENGTH: 64
<212> TYPE: DNA
<213> ORGANISM: Artificial Sequence
<220> FEATURE:
<223> OTHER INFORMATION: Synthetic Construct

<400> SEQUENCE: 3
cagaagctaa tgctaatgta ctactactac tactactacc cacgcttttt ctaatcatat    60
tttc                                                                 64

<210> SEQ ID NO 4
<211> LENGTH: 29
<212> TYPE: DNA
<213> ORGANISM: Artificial Sequence
<220> FEATURE:
<223> OTHER INFORMATION: Synthetic Construct

<400> SEQUENCE: 4
ttgttatatt ttaagatgta gtagtagta                                      29

METHODS AND PROBES FOR DETECTION AND/OR QUANTIFICATION OF NUCLEIC ACID SEQUENCES

CROSS-REFERENCE TO RELATED APPLICATIONS

This application claims the priority benefit of the provisional patent application U.S. Ser. No. 60/238,850, filed Oct. 6, 2000, which is incorporated by reference in its entirety.

TECHNICAL FIELD

The invention relates to detection and/or quantification of nucleic acid sequences using nucleic acid detector probes.

BACKGROUND ART

The development of nucleic acid amplification methods contributed to the rapid advances in genome research, biotechnology, molecular medicine, and the like. Rapid methods for the detection and quantification of specific nucleic acid sequences, either directly or following amplification, are required for nucleic acid analysis as used in various research, clinical and industrial applications. Various homogenous or heterogeneous methods for the detection of binding of the one or more labels to the target sequence were described.

Nucleic acid hybridization is commonly used for the detection of specific sequences. Methods for the detection and quantification of nucleic acid sequences, which utilize hybridization of one or more oligonucleotide probes to a specific target sequence, usually employ means of detection of hybrid formation. Some methods utilize one or more labeled probes that are complementary to a specific region of the target nucleic acid sequence, and means of detecting binding of the one or more labels to the target sequence.

Some of the previously described detection methods employ enzyme-catalyzed reactions. These methods are based on detection of the formation of hybrids of the specific target nucleic acid and one or more oligonucleotide probes, which may be labeled. Both enzymatic cleavage and ligation of specific oligonucleotide probes hybridized to target nucleic acid sequence have been described. The enzymatic reaction products are detected directly, for example, by changes of optical properties of the labels, or by their capacity to induce additional enzymatic reaction or become substrates for additional enzymes. The enzyme-based detection methods may be employed either for the direct detection of specific nucleic acid sequences, or may be employed for the detection of amplification products. Some of the commonly used homogeneous detection methods employing enzymes which cleave oligonucleotide probes when bound to the target nucleic acid sequence by hybridization, are CYCLING PROBE METHOD™, TAQMAN™, INVADER™, and the like. Many of these methods employ an oligonucleotide which is labeled with a pair of a fluorescent and a quencher labels, which are attached to the probe at the correct distance to ensure energy transfer from the fluorescent label to the quencher label. Cleavage of one of the probes when hybridized to the target nucleic acid sequence results in separation of the two labels which results in the generation of fluorescent signal. Various modifications of this principle have been described (Nurmi et al., 2000, Nucleic acid Res. 28, 28e; U.S. Pat. No. 5,403,711 (Walder); Nadeau et al., 1999, Anal Biochem 276: 177).

Other methods employ means of direct, non-enzymatic, detection of one or more probe-target hybrid formation. Both homogeneous and heterogeneous detection methods have been described. Heterogeneous detection methods that require extensive wash steps are inherently more complicated and are less desirable. Homogeneous detection methods are faster and are better suited for applications requiring high throughput. Hybridization of one or more labeled probes to a specific target nucleic acid sequence may result in changes in the optical properties of the one or more labeled probes. Alternatively, the association of two or more labels in a stable complex, as a result of hybridization of two or more oligonucleotide probes to a single nucleic acid target, can be detected.

Homogeneous detection of hybrid formation based on the separation of donor-acceptor label molecules has been described recently. A method utilizing a change in probe conformation upon hybridization to a target nucleic acid sequence thereby changing the distance of donor acceptor label molecules, was described by Tyagi et al. (U.S. Pat. No. 5,925,517). The probe is composed of a stem loop structure, which brings the donor-acceptor pair of labels attached to the probe in close proximity to effect fluorescence quenching. Hybridization of the probe to a specific target nucleic acid sequence results in a conformational change which is characterized by dissociation of the stem structure thereby increasing the distance between the two labels and preventing energy transfer between the two labels. Thus, hybridization of the oligonucleotide to the specific target nucleic acid sequence is detectable by a fluorescence signal of the donor label. Other variations on this concept have also been disclosed. Detection of nucleic acid by fluorescence quenching was also described by Bruce et al (EP patent application no. 98117883.3). The detector oligonucleotide probe comprises at least two oligonucleotides, which hybridize to form a partially double stranded detector. Acceptor and donor dyes are attached to the detector oligonucleotides so as to place them at close proximity to enable energy transfer. Upon hybridization of the single stranded portion of the detector probe to the target nucleic acid sequence the second oligonucleotide probe is displaced from the first oligonucleotide probe, thus increasing the distance between the donor and acceptor dye labels, causing a change in fluorescence that is detectable.

There is a need for improved nucleic acid detection and/or quantification methods. The invention provided herein fulfills this need and also provides additional benefits. These include the ease of preparation of the detector probes. The design of the interacting sequences of the detector probes are independent of the target sequence and could thus be universal. Insofar as the detector probes are not unimolecular, the design complexities of a stem loop probe are eliminated.

All references cited herein, including patent applications and publications, are incorporated by reference in their entirety.

DISCLOSURE OF THE INVENTION

In one aspect of the present invention, detector oligonucleotide probes which are useful for the detection of a specific nucleic acid sequence are provided. A first oligonucleotide probe comprises a 3'-region that is hybridizable to a sequence of the target nucleic acid; a 5'-region that is not hybridizable to the target nucleic acid (under otherwise same hybridization conditions as described herein), and a label (F) that is attached to the 5'-end. A second oligonucleotide probe comprises a 5'-region, which is hybridizable to a sequence of the target nucleic acid and a 3'-region, which is not hybridizable to the target nucleic acid (under otherwise same hybridization conditions as described herein), and is hybridizable to part of the sequence of the first oligonucleotide which is not hybridizable to the target nucleic acid. A third oligonucleotide probe comprises a sequence which is not hybridizable to the target nucleic acid sequence and is hybridizable to the 5'-most sequence of the first oligonucleotide, and a label Q that is attached to its 3'-end. In some embodiments, probes with the mirror image design of the preceding oligonucleotide probes are provided. In some embodiments, a single oligonucleotide probe comprises both labels and the functions of either the first and third oligonucleotide probe, or the second and third oligonucleotide probe. Mirror images (i.e., the opposite polarity) of the probes are also provided.

In another aspect of the present invention, methods for detecting and/or quantifying nucleic acid sequences are provided using the probes described above. Detection of a target nucleic acid according to the methods of the invention comprises a) combining a sample suspected of containing said target nucleic acid sequence with a mixture containing the probes described above; optionally b) treating the mixture to render the target nucleic acid single stranded (if not already single stranded); and c) incubating the mixture under conditions which are suitable for binding of the oligonucleotide probes to said single stranded nucleic acid target, wherein binding of the first and second probes to the nucleic acid target results in the displacement of the third probe from the first probe, wherein said displacement results in the spatial separation of the labels of the first probe and the third probe, whereby a detectable and/or quantifiable signal is generated.

In another aspect of the present invention, a method of determining whether a target nucleic acid sequence is present in a sample is provided, comprising: contacting said sample with a first probe, a second probe, and a third probe, under conditions allowing hybridization of the first and second probes to the target nucleic acid sequence, if present, and hybridization of the first probe to the third probe, in the absence of the target nucleic acid sequence, and hybridization of the second probe to the first probe when the second probe is hybridized to the target nucleic acid sequence, wherein: the first probe comprises a polynucleotide comprising a 3' region which hybridizes to a first region of the target nucleic acid sequence, if present, and a first member of an interacting label pair; the second probe comprises a polynucleotide comprising a 5' region which hybridizes to a second region of the target nucleic acid sequence, if present, and a 3' region which hybridizes to a sequence in the 5' region of the first probe, if the target nucleic acid sequence is present; and the third probe comprises a polynucleotide which hybridizes to a sequence in the 5' region of the first probe, and a second member of an interacting label pair; wherein when said third probe is hybridized to said first probe, said first and second members of the interacting label pair are brought into proximity and interact; and wherein, in the presence of the target nucleic acid sequence, said 3' region of said first probe hybridizes to said first region of the target nucleic acid sequence and said 5' region of said second probe hybridizes to said second region of the target nucleic acid sequence and said 3' region of said second probe hybridizes to the first probe, causing dissociation of the first and second members of the interacting label pair; whereby generation of a detectable signal caused by dissociation of the interacting label pair indicates presence of the target nucleic acid sequence. This aspect may further comprise extension of the 3' end of the second probe along a sequence in the 5' region of the first probe using a nucleotide polymerase.

In a further aspect of the present invention is provided a method of determining whether a target nucleic acid sequence is present in a sample, comprising: contacting said sample with a first probe, a second probe, and a third probe, under conditions allowing hybridization of the first and second probes to the target nucleic acid sequence, if present, and hybridization of the first probe to the third probe, in the absence of the target nucleic acid sequence, and hybridization of the second probe to the first probe when the second probe is hybridized to the target nucleic acid sequence, wherein the first probe comprises a polynucleotide comprising a 5' region which hybridizes to a first region of the target nucleic acid sequence, if present, and a first member of an interacting label pair; the second probe comprises a polynucleotide comprising a 3' region which hybridizes to a second region of the target nucleic acid sequence, if present, and a 5' region which hybridizes to a sequence in the 3' region of the first probe, if the target nucleic acid sequence is present; and the third probe comprises a polynucleotide which hybridizes to a sequence in the 3' region of the first probe, and a second member of an interacting label pair; wherein when said third probe is hybridized to said first probe, said first and second members of the interacting label pair are brought into proximity and interact; and wherein, in the presence of the target nucleic acid sequence, said 5' region of said first probe hybridizes to said first region of the target nucleic acid sequence and said 3' region of said second probe hybridizes to said second region of the target nucleic acid sequence and said 5' region of said second probe hybridizes to the first probe, causing dissociation of the first and second members of the interacting label pair; whereby generation of a detectable signal caused by dissociation of the interacting label pair indicates presence of the target nucleic acid sequence.

In the methods of the invention, the first and second regions of the target nucleic acid sequence may be contiguous, 1 nucleotide apart, 3 or fewer nucleotides apart, or 7 or fewer nucleotides apart. In addition, the interacting label pair may comprise donor and acceptor moieties, or the interacting label pair may comprises an enzyme, such as an enzyme and an inhibitor of said enzyme, or the interacting label pair may be capable of energy transfer, for example the interacting label pair may comprise a fluorophore and a quencher.

The methods may further comprise measuring the magnitude of the signal generated, whereby said magnitude indicates the quantity of the target nucleic acid sequence.

The target nucleic acid sequence may be attached to an analyte, or to a solid support. The target nucleic acid sequence may comprise DNA, RNA, DNA and RNA, or PNA. At least one of the probes may comprise DNA, RNA, DNA and RNA or PNA. The region of the second probe which is hybridizable to a sequence of the first probe may comprise a modified nucleotide that causes enhanced affinity to the sequence in the region of the first probe relative to an unmodified nucleotide. In one aspect, the detectable signal is of a greater magnitude than a detectable signal associated with the interacting label pair when the third probe is hybridized to the first probe. In another aspect, the detectable signal is of a lesser magnitude than a detectable signal associated with the interacting label pair when the third probe is hybridized to the first probe. In a further aspect, the method further comprises amplifying the target nucleic acid sequence. In yet a further aspect, the first probe or the second probe is allele-specific. In a still further aspect, the first probe and the second probe are allele-specific.

In a further aspect, the invention provides a method of determining whether a target nucleic acid sequence is present in a sample, comprising: contacting said sample with a first probe, a second probe, a third probe, and a nucleotide polymerase, under conditions allowing hybridization of the first and second probes to the target nucleic acid sequence, if present, and hybridization of the first probe to the third probe, in the absence of the target nucleic acid sequence, and allowing nucleic acid polymerization, wherein: the first probe comprises a polynucleotide comprising a 3' region which hybridizes to a first region of the target nucleic acid sequence, if present, a first member of an interacting label pair; and the second probe comprises a polynucleotide comprising a 5' region which hybridizes to a second region of the target nucleic acid sequence, if present; and the third probe comprises a polynucleotide sequence which hybridizes to a sequence in the 5' region of the first probe, and a second member of an interacting label pair; wherein when said third probe is hybridized to said first probe, said first and second members of the interacting label pair are brought into proximity and interact; and wherein, in the presence of the target nucleic acid sequence, said 3' region of said first probe hybridizes to said first region of the target nucleic acid sequence and said 5' region of said second probe hybridizes to said second region of the target nucleic acid sequence; and wherein the 3' end of said second probe is extended by said nucleotide polymerase along the first probe by template switching, causing dissociation of the first and second members of the interacting label pair; whereby generation of detectable signal caused by dissociation of the interacting label pair indicates presence of the target nucleic acid sequence.

In a further aspect, the invention provides a method of determining whether a target nucleic acid sequence is present in a sample, said method comprising: contacting said sample with a first probe and a second probe, under conditions allowing hybridization of the first and second probes to the target nucleic acid sequence, if present, and hybridization of a first nucleotide sequence in the 5' region of the first probe with a second nucleotide sequence in the 5' region of the first probe, in the absence of the target nucleic acid sequence, and hybridization of at the second probe the first probe when the second probe is hybridized to the target nucleic acid sequence, wherein: the first probe comprises a polynucleotide comprising a 3' region which hybridizes to a first region of the target nucleic acid sequence, if present, and a 5' region comprising said first and second nucleotide sequences which hybridize to each other in the absence of the target nucleic acid sequence, and two members of an interacting label pair; the second probe comprises a polynucleotide comprising a 5' region which hybridizes to a second region of the target nucleic acid sequence, if present and a 3' region which hybridizes to a sequence in the 5' region of the first probe, if the target polynucleotide is present; wherein, when said first and second nucleotide sequences in the 5' region of the first probe hybridize, said first and second members of the interacting label pair are brought into proximity and interact; and wherein, in the presence of the target nucleic acid sequence, said first probe and said second probe hybridize to the target nucleic acid sequence and said second probe hybridizes to the first probe, causing dissociation of the first and second members of the interacting label pair; whereby generation of detectable signal caused by dissociation of the interacting label pair indicates presence of the target nucleic acid sequence.

In yet further aspect, the invention provides a method of determining whether a target nucleic acid sequence is present in a sample, said method comprising: contacting said sample with a first probe and a second probe, under conditions allowing hybridization of the first and second probes to the target nucleic acid sequence, if present, and hybridization of a first nucleotide sequence in the 3' region of the first probe with a second nucleotide sequence in the 3' region of the first probe, in the absence of the target nucleic acid sequence, and hybridization of at the second probe the first probe when the second probe is hybridized to the target nucleic acid sequence, wherein: the first probe comprises a polynucleotide comprising a 5' region which is hybridizes to a first region of the target nucleic acid sequence, if present, and a 3' region comprising said first and second nucleotide sequences which hybridize to each other in the absence of the target nucleic acid sequence, and two members of an interacting label pair; the second probe comprises a polynucleotide comprising a 3' region which hybridizes to a second region of the target nucleic acid sequence, if present and a 5' region which hybridizes to a sequence in the 3' region of the first probe, if the target polynucleotide is present; wherein, when said first and second nucleotide sequences in the 3' region of the first probe hybridize, said first and second members of the interacting label pair are brought into proximity and interact; and wherein, in the presence of the target nucleic acid sequence, said first probe and said second probe hybridize to the target nucleic acid sequence and said second probe hybridizes to the first probe, causing dissociation of the first and second members of the interacting label pair; whereby generation of detectable signal caused by dissociation of the interacting label pair indicates presence of the target nucleic acid sequence.

In yet another aspect of the present invention, methods for detecting changes, or mutations, in a sequence of the target nucleic acid relative to a reference nucleic acid sequence (unaltered target sequence), are provided. In one embodiment, detection of altered sequence in a target nucleic acid according to the methods of the invention comprises a) combining a test sample suspected of containing said target nucleic acid sequence (with suspected altered target sequence) with a mixture containing the probes described above, wherein the first and/or third oligonucleotide probes comprise a sequence hybridizable to the unaltered (reference) target sequence; optionally b) treating the mixture to render the target nucleic acid single stranded (if not already single stranded); and c) incubating the mixture under conditions which are suitable for binding of the oligonucleotide probes to said single stranded nucleic acid target, wherein binding of the first and second probes to the nucleic acid target results in the displacement of the third probe from the first probe, wherein said displacement results in the spatial separation of the labels of the first probe and the third probe, whereby a detectable and/or quantifiable signal is generated. In this embodiment, reduction or elimination of detectable signal in the test sample (relative to a reference sample comprising unaltered target (reference) sequence) indicates reduced or no binding of the probe(s) to the nucleic acid target in the test sample, which indicates presence of the altered sequence in the test sample. In another embodiment, detection of altered sequence in a target nucleic acid according to the methods of the invention comprises a) combining a test sample suspected of containing said target nucleic acid sequence (with suspected altered target sequence) with a mixture containing the probes described above, wherein the first and/or third oligonucleotide probes comprise a sequence hybridizable to the suspected altered target sequence; optionally b) treating the mixture to render the target nucleic acid single stranded (if not already single stranded); and c) incubating the mixture under conditions which are suitable for binding of the oligonucleotide probes to said single stranded nucleic acid target, wherein binding of the first and second probes to the nucleic acid target results in the displacement of the third probe from the first probe, wherein said displacement results in the spatial separation of the labels of the first probe and the third probe, whereby a detectable and/or quantifiable signal is generated. In this embodiment, a greater amount of detectable signal in the test sample (relative to a reference sample comprising unaltered (reference) sequence) indicates more binding of the probe(s) to the nucleic acid target in the test sample, which indicates presence of the altered sequence in the test sample.

A further aspect of the present invention provides a method of determining whether a target nucleic acid sequence contains a sequence alteration relative to a reference nucleic acid sequence, said method comprising: contacting said target nucleic acid sequence with a first probe, a second probe, and a third probe, and contacting said reference nucleic acid sequence with a first probe, a second probe, and a third probe, wherein said contact of the target nucleic acid sequence with the first, second, and third probes, and said contact of the reference nucleic acid sequence with the first, second, and third probes, occur under conditions allowing hybridization of the first and second probes to the reference nucleic acid sequence, and hybridization of the first probe to the third probe, in the absence of the reference nucleic acid sequence, and hybridization of the second probe to the first probe when the second probe is hybridized to the reference nucleic acid sequence, wherein the first probe comprises a polynucleotide comprising a 3' region which hybridizes to a first region of the reference nucleic acid sequence, if present, and a first member of an interacting label pair; the second probe comprises a polynucleotide comprising a 5' region which hybridizes to a second region of the reference nucleic acid sequence, if present, and a 3' region which hybridizes to a sequence in the 5' region of the first probe, if the reference nucleic acid sequence is present; and the third probe comprises a polynucleotide which hybridizes to a sequence in the 5' region of the first probe, and a second member of an interacting label pair; wherein when said third probe is hybridized to said first probe, said first and second members of the interacting label pair are brought into proximity and interact; and wherein, in the presence of the reference nucleic acid sequence, said 3' region of said first probe hybridizes to said first region of the reference nucleic acid sequence and said 5' region of said second probe hybridizes to said second region of the reference nucleic acid sequence and said 3' region of said second probe hybridizes to the first probe, causing dissociation of the first and second members of the interacting label pair; and comparing detectable signal generated by contacting said first, second, and third probes with the reference nucleic acid sequence with detectable signal generated by contacting said first, second, and third probes with target nucleic acid sequence; whereby reduced signal generation by the target nucleic acid sequence as compared to the reference nucleic acid sequence indicates the presence of an altered sequence in the target nucleic acid sequence relative to the reference nucleic acid sequence.

In yet a further aspect, the present invention provides a method of determining whether a target nucleic acid sequence contains a sequence alteration relative to a reference nucleic acid sequence, said method comprising: contacting said target nucleic acid sequence with a first probe, a second probe, and a third probe, and contacting said reference nucleic acid sequence with a first probe, a second probe, and a third probe, wherein said contact of the target nucleic acid sequence with the first, second, and third probes, and said contact of the reference nucleic acid sequence with the first, second, and third probes, occur under conditions allowing hybridization of the first and second probes to the reference nucleic acid sequence, and hybridization of the first probe to the third probe, in the absence of the reference nucleic acid sequence, and hybridization of the second probe to the first probe when the second probe is hybridized to the reference nucleic acid sequence, wherein the first probe comprises a polynucleotide comprising a 5' region which hybridizes to a first region of the reference nucleic acid sequence, if present, and a first member of an interacting label pair; the second probe comprises a polynucleotide comprising a 3' region which hybridizes to a second region of the reference nucleic acid sequence, if present, and a 5' region which hybridizes to a sequence in the 3' region of the first probe, if the reference nucleic acid sequence is present; and the third probe comprises a polynucleotide which hybridizes to a sequence in the 5' region of the first probe, and a second member of an interacting label pair; wherein when said third probe is hybridized to said first probe, said first and second members of the interacting label pair are brought into proximity and interact; and wherein, in the presence of the reference nucleic acid sequence, said 5' region of said first probe hybridizes to said first region of the reference nucleic acid sequence and said 3' region of said second probe hybridizes to said second region of the reference nucleic acid sequence and said 5' region of said second probe hybridizes to the first probe, causing dissociation of the first and second members of the interacting label pair; and comparing detectable signal generated by contacting said first, second, and third probes with the reference nucleic acid sequence with detectable signal generated by contacting said first, second, and third probes with target nucleic acid sequence; whereby reduced signal generation by the target nucleic acid sequence as compared to the reference nucleic acid sequence indicates the presence of an altered sequence in the target nucleic acid sequence relative to the reference nucleic acid sequence.

As is evident to one skilled in the art, in these methods binding of first and second probes to the target nucleic acid sequence competes with binding of the third probe to the second probe, thus maintaining the spatial separation of the labels of the first probe and the third probe, whereby a detectable and/or quantifiable signal is generated .

In another aspect of the present invention, methods for genotype determination are provided. In these methods, the first and/or third oligonucleotide probes that are allele-specific are used.

Another aspect of the invention provides methods of detection and/or quantification of multiple target nucleic acid sequences in a sample. In these methods, two or more combinations (pairs) of interacting labels, each pair specific for a defined target nucleic acid sequence, are used.

Accordingly, the invention provides a method of determining whether one or more of a plurality of target nucleic acid sequences is present in a sample, comprising: contacting said sample with a plurality of probe sets, each set comprising a first probe, a second probe, and a third probe, under conditions allowing hybridization of the first and second probes to a target nucleic acid sequence, if present, and hybridization of the first probe to the third probe, in the absence of said target nucleic acid sequence, and hybridization of the second probe to the first probe when the second probe is hybridized to said target nucleic acid sequence, wherein the first probe comprises a polynucleotide comprising a 3' region which hybridizes to a first region of said target nucleic acid sequence, if present, and a first member of an interacting label pair; the second probe comprises a polynucleotide comprising a 5' region which hybridizes to a second region of said target nucleic acid sequence, if present, and a 3' region which hybridizes to a sequence in the 5' region of the first probe, if said target nucleic acid sequence is present; the third probe comprises a polynucleotide which hybridizes to a sequence in the 5' region of the first probe, and a second member of an interacting label pair; wherein when said third probe is hybridized to said first probe, said first and second members of the interacting label pair are brought into proximity and interact; and wherein, in the presence of said target nucleic acid sequence, said 3' region of said first probe hybridizes to said first region of said target nucleic acid sequence and said 5' region of said second probe hybridizes to said second region of said target nucleic acid sequence and said 3' region of said second probe hybridizes to the first probe, causing dissociation of the first and second members of the interacting label pair; whereby generation of a detectable signal caused by dissociation of the interacting label pair indicates presence of said target nucleic acid sequence; and wherein each probe set comprises an interacting label pair which generates a detectable signal which is different from the signals of the interacting label pairs of every other probe set, and generation of two or more signals indicates presence of a plurality of target nucleic acid sequences.

In another aspect, the invention provides a method of determining whether one or more of a plurality of target nucleic acid sequences is present in a sample, comprising: contacting said sample with a plurality of probe sets, each set comprising a first probe, a second probe, and a third probe, under conditions allowing hybridization of the first and second probes to a target nucleic acid sequence, if present, and hybridization of the first probe to the third probe, in the absence of said target nucleic acid sequence, and hybridization of the second probe to the first probe when the second probe is hybridized to said target nucleic acid sequence, wherein the first probe comprises a polynucleotide comprising a 5' region which hybridizes to a first region of said target nucleic acid sequence, if present, and a first member of an interacting label pair; the second probe comprises a polynucleotide comprising a 3' region which hybridizes to a second region of said target nucleic acid sequence, if present, and a 5' region which hybridizes to a sequence in the 3' region of the first probe, if said target nucleic acid sequence is present; the third probe comprises a polynucleotide which hybridizes to a sequence in the 3' region of the first probe, and a second member of an interacting label pair; wherein when said third probe is hybridized to said first probe, said first and second members of the interacting label pair are brought into proximity and interact; and wherein, in the presence of said target nucleic acid sequence, said 5' region of said first probe hybridizes to said first region of said target nucleic acid sequence and said 3' region of said second probe hybridizes to said second region of said target nucleic acid sequence and said 5' region of said second probe hybridizes to the first probe, causing dissociation of the first and second members of the interacting label pair; whereby generation of a detectable signal caused by dissociation of the interacting label pair indicates presence of said target nucleic acid sequence; and wherein each probe set comprises an interacting label pair which generates a detectable signal which is different from the signals of the interacting label pairs of every other probe set, and generation of two or more signals indicates presence of a plurality of target nucleic acid sequences.

The invention also provides compositions, kits, complexes, reaction mixtures and systems comprising various components (and various combinations of the components) used in the methods described herein.

In one aspect, the invention provides a composition comprising a first probe, a second probe and a third probe, wherein the first probe comprises a polynucleotide comprising a 3' region which hybridizes to a first region of a target nucleic acid sequence, if present, and a first member of an interacting label pair; the second probe comprises a polynucleotide comprising a 5' region which hybridizes to a second region of the target nucleic acid sequence, if present, and a 3' region which hybridizes to a sequence in the 5' region of the first probe, if the target nucleic acid sequence is present; the third probe comprises a polynucleotide which hybridizes to a sequence in the 5' region of the first probe, and a second member of an interacting label pair; wherein when said third probe is hybridized to said first probe, said first and second members of the interacting label pair are brought into proximity and interact; and wherein, in the presence of the target nucleic acid sequence, said 3' region of said first probe hybridizes to said first region of the target nucleic acid sequence and said 5' region of said second probe hybridizes to said second region of the target nucleic acid sequence and said 3' region of said second probe hybridizes to the first probe, causing dissociation of the first and second members of the interacting label pair; whereby generation of a detectable signal caused by dissociation of the interacting label pair indicates presence of the target nucleic acid sequence.

In another aspect, the invention provides a composition comprising a first probe, a second probe and a third probe, wherein the first probe comprises a polynucleotide comprising a 5' region which hybridizes to a first region of a target nucleic acid sequence, if present, and a first member of an interacting label pair; the second probe comprises a polynucleotide comprising a 3' region which hybridizes to a second region of the target nucleic acid sequence, if present, and a 5' region which hybridizes to a sequence in the 3' region of the first probe, if the target nucleic acid sequence is present; the third probe comprises a polynucleotide which hybridizes to a sequence in the 3' region of the first probe, and a second member of an interacting label pair; wherein when said third probe is hybridized to said first probe, said first and second members of the interacting label pair are brought into proximity and interact; and wherein, in the presence of the target nucleic acid sequence, said 5' region of said first probe hybridizes to said first region of the target nucleic acid sequence and said 3' region of said second probe hybridizes to said second region of the target nucleic acid sequence and said 5' region of said second probe hybridizes to the first probe, causing dissociation of the first and second members of the interacting label pair; whereby generation of a detectable signal caused by dissociation of the interacting label pair indicates presence of the target nucleic acid sequence.

The compositions may comprise an interacting moiety pair which comprises a fluorophore and a quencher. The compositions may further comprise a nucleotide polymerase the target nucleic acid sequence, and/or a reference nucleic acid sequence to which the target nucleic acid sequence is to be compared.

In another aspect, the invention provides kits for conducting the methods described herein. These kits, in suitable packaging and generally (but not necessarily) containing suitable instructions, contain one or more components used in the detection and/or quantification methods.

In one aspect, the invention provides a kit for determining whether a target nucleic acid is present in a sample or quantifying a target nucleic acid sequence, comprising a first probe, a second probe and a third probe, wherein the first probe comprises a polynucleotide comprising a 3' region which hybridizes to a first region of a target nucleic acid sequence, if present, and a first member of an interacting label pair; the second probe comprises a polynucleotide comprising a 5' region which hybridizes to a second region of the target nucleic acid sequence, if present, and a 3' region which hybridizes to a sequence in the 5' region of the first probe, if the target nucleic acid sequence is present; and the third probe comprises a polynucleotide which hybridizes to a sequence in the 5' region of the first probe, and a second member of an interacting label pair; wherein when said third probe is hybridized to said first probe, said first and second members of the interacting label pair are brought into proximity and interact; and wherein, in the presence of the target nucleic acid sequence, said 3' region of said first probe hybridizes to said first region of the target nucleic acid sequence and said 5' region of said second probe hybridizes to said second region of the target nucleic acid sequence and said 3' region of said second probe hybridizes to the first probe, causing dissociation of the first and second members of the interacting label pair; whereby generation of a detectable signal caused by dissociation of the interacting label pair indicates presence of the target nucleic acid sequence.

In a further aspect, the invention provides a kit for determining whether a target nucleic acid is present in a sample or quantifying a target nucleic acid sequence, comprising a first probe, a second probe and a third probe, wherein the first probe comprises a polynucleotide comprising a 5' region which hybridizes to a first region of a target nucleic acid sequence, if present, and a first member of an interacting label pair; the second probe comprises a polynucleotide comprising a 3' region which hybridizes to a second region of the target nucleic acid sequence, if present, and a 5' region which hybridizes to a sequence in the 3' region of the first probe, if the target nucleic acid sequence is present; the third probe comprises a polynucleotide which hybridizes to a sequence in the 3' region of the first probe, and a second member of an interacting label pair; wherein when said third probe is hybridized to said first probe, said first and second members of the interacting label pair are brought into proximity and interact; and wherein, in the presence of the target nucleic acid sequence, said 5' region of said first probe hybridizes to said first region of the target nucleic acid sequence and said 3' region of said second probe hybridizes to said second region of the target nucleic acid sequence and said 5' region of said second probe hybridizes to the first probe, causing dissociation of the first and second members of the interacting label pair; whereby generation of a detectable signal caused by dissociation of the interacting label pair indicates presence of the target nucleic acid sequence.

Kits of the invention may further comprise a reference nucleic acid sequence to which the target nucleic acid sequence may be compared, and/or instructions for use of the kit to determine the presence of the target nucleic acid sequence in a sample or quantify the target nucleic acid sequence.

In another aspect, the invention provides compositions comprising any of the complexes (which are generally considered as intermediates with respect to the final products) described herein (see also the figures for schematic depictions of these various complexes).

In another aspect, the invention provides reaction mixtures (or compositions comprising reaction mixtures) which contain various combinations of components described herein.

In another aspect, the invention provides systems for effecting the detection and/or quantification methods described herein.

BRIEF DESCRIPTION OF THE DRAWINGS

FIG. 1a), probe B (second oligonucleotide; FIG. 1b) and probe C (third oligonucleotide; FIG. 1c). As an example of an interacting label pair, "F" and "Q" are labels, such as, for example, a fluorophore and a quencher.

FIG. 6 is a schematic representation of the mirror image design of probe A (FIG. 6a), probe B (FIG. 6b), and probe C (FIG. 6c), depicted in the preceding figures. As an example of an interacting label pair, "F" and "Q" are labels, such as, for example, a fluorophore and a quencher.

MODES FOR CARRYING OUT THE INVENTION

Figure 1:
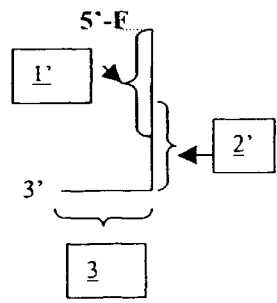
FIG. 1 is a schematic representation of probe A (first oligonucleotide.
Figure 1:
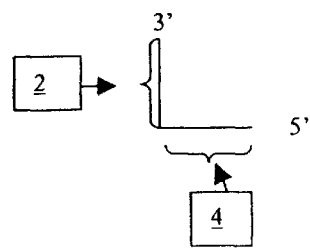
Figure 1:
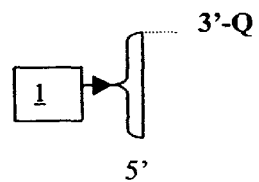

The present invention discloses detector oligonucleotide probes for detection and/or quantification of target nucleic acid sequences, and detection and/or quantification methods using the probes. In the absence of target nucleic acid sequence, a first oligonucleotide and a third oligonucleotide are bound to each other in a conformation which brings members of an interacting label pair into a sufficiently close spatial proximity that the members of the pair interact. Cooperative binding of the first oligonucleotide and a second oligonucleotide to a target polynucleotide, optionally followed by polymerase-catalyzed extension of the second oligonucleotide, effects (a) displacement of the third oligonucleotide from the first oligonucleotide probe resulting in dissociation (separation) of the members of the interacting label pair, and/or (b) competition with binding of the third probe to the second probe, thus maintaining the spatial separation of the labels of the first probe and the third probe, whereby a detectable and/or quantifiable signal is generated. The spatial separation of the members of the interacting label pair (labels) is detectable, and is indicative of the presence and/or amount of the target nucleic acid sequence. Thus, the methods are useful for detection and/or quantification of a specific nucleic acid sequence as well as the detection of sequence alterations in a target nucleic acid sequence.

A variety of interacting label pairs (labels) can be used in methods and probes of the invention. Detectable signals indicative of separation of the members of the interacting label pair can be achieved in a number of ways, as is known in the art. As discussed herein, generating a signal includes any of increase, alteration, dampening or reduction, and/or elimination of a signal. For example, in some embodiments, generation of a detectable signal is dependent on changes in the spectroscopic properties of the members of the interacting label pair, wherein the spectroscopic properties are affected by the spatial proximity of the members of the interacting label pair. In other embodiments, members (labels) possess donor and acceptor properties, respectively, wherein said donor and acceptor properties are affected by the spatial proximity of the labels. Donor and acceptors generally refer to dye labels or other energy transfer pairs. In other embodiments, members may be any interacting pair that generates a signal when separated, for example, an enzyme-inhibitor pair or allosteric enzyme-suppressor pair. Signal detection may be direct or indirect.

The target nucleic acid sequence may be directly detected by the methods of the invention or may be first amplified by any of a variety of nucleic acid amplification methods known in the art.

The present invention provides numerous advantages over previously described detection and/or quantification methods. For example, the advantages of the present invention include the ease of preparation of the detector probes. The design of the interacting sequences of the detector probes is independent of the target polynucleotide sequence and could thus be universal. Insofar as the detector probes are not unimolecular, the design complexities of stem loop probes such as those known in the art are eliminated.

The methods of the invention may be used to detect and quantify target nucleic acid sequences, or determine whether a target nucleic acid is present in a sample. The methods may also be used to detect changes in target nucleic acid sequences, for example, mutations (including single nucleotide mutations), or, for example, polymorphisms. The methods may also be used to detect and quantify multiple target nucleic acid sequences.

In addition, the methods of the invention may be used in conjunction with nucleic acid amplification techniques to detect, quantify, and/or verify fidelity of amplification. The methods may be used in real time; i.e., simultaneously with amplification, in the same reaction mixture. The method may further be used for signal generation for the quantification of an analyte (i.e., a moiety other than the target nucleic acid sequence to be detected) in a sample. A known nucleic acid sequence may be attached to one member of a specific binding pair. The specific binding pair (SBP) comprises a first member of the SBP that is an analyte to be tested and the second member of the SBP is a molecular species, such as an antibody, which can specifically bind to the first member of the SBP. The second member of the SBP may be labeled by attachment of the known nucleic acid sequence. Following binding of the members of the SBP, the complex may be detected and quantified by probes and method of the invention.

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

Probe, oligonucleotides and polynucleotides employed in the present invention can be generated using standard techniques known in the art.

Definitions

The "target nucleic acid sequence," or sequences, or "target nucleic acid," or "target polynucleotide" (all of which are used interchangeably herein) may be any nucleic acid sequence(s) the presence and/or amount of which is desired to be known. In some embodiments, the sequence of the target nucleic acid is known. In some embodiments, e.g., mutation detection, the target nucleic acid sequence may be a sequence which is suspected of having alterations (i.e., differences) from a reference nucleic acid sequence. In these embodiments, the sequence of the target nucleic acid may or may not be known, and the "reference nucleic acid sequence" is a nucleic acid whose sequence is known and to which the target nucleic acid sequence or sequences may be compared, e.g., a wild-type sequence. In this case, the alteration in the target nucleic acid may be in a single nucleotide base or more than a single nucleotide base. Such an altered sequence can be a known polymorphic sequence, including, for example, single nucleotide polymorphism.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O) R, P(O)OR', CO or CH$_2$ ("formacetal"), in which each R or R' is independently H or substituted or unsubstituted alkyl (1–20 C) optionally containing an ether (—O—) linkage, aryl, alkenyl, cycloalkyl, cycloalkenyl or araldyl. In addition, "polynucleotides" include peptide nucleic acid (PNA), lacking pentose sugar phosphate groups, in which the monomeric unit is 2-aminoethyl glycine linked by a methylenecarbonyl linkage to a base found in DNA. Not all linkages in a polynucleotide need be identical. The preceding description applies to all polynucleotides referred to herein, including RNA, DNA, and PNA, as appropriate.

"Hybridizable," as used herein, refers to the capability of two polynucleotide sequences to hybridize through complementary base pairing, under conditions used in an assay described herein; i.e., at the temperature, pH, ionic concentrations, and the like, used in carrying out the methods of the invention. "Mutually hybridizable" refers to two polynucleotide sequences that are capable of hybridizing under the conditions used in the assay.

An "interacting label pair," as used herein, refers to two members whose ability to interact with each other is dependent on their proximity to each other, wherein said interaction results in generation of a detectable signal indicative of the proximity of the moieties to each other. For example, when moieties (members) of an interacting label pair are placed in sufficient proximity to each other, they are capable of generating a detectable signal that is distinguishable from a signal associated with said moieties when not placed in said sufficient proximity. The signal generated (or generation of a signal) may be an increase in some measurable characteristic or a decrease in some measurable characteristic. An interacting label pair generally comprises two interacting moieties. However, each moiety or member of an interacting label pair may comprise more than one moiety or member. Interacting label pairs are known in the art, and described herein, for example, fluorescent dye-quencher, and receptor-ligand.

By "dissociation" is meant lessening or reduction of the proximity of the members of the interacting label pair, including but not limited to separation of the two members, or failure of the two members to associate, which in turn arises from probes binding to the target nucleic acid sequence, such that detectable signal is generated (as generally compared to signal arising from interaction of the label pairs)—i.e., such that activity caused by proximate association (interaction) is affected. The signal generated (or generation of a signal) may be an increase in some measurable characteristic or a decrease in some measurable characteristic. The terms "dissociation" and "separation" and "dissociate" and "separate" are used interchangeably herein.

By "signal" is meant a measurable characteristic. The signal may increase or decrease upon dissociation of the members of the interacting label pair. For example, if the interacting label pair comprises a fluorophore and a quencher, dissociation of the members of the pair generates a detectable signal due to an increase in light energy emitted by the fluorophore in response to illumination. Or, for example, if the interacting label pair comprises subunits of an enzyme, dissociation of the members of the pair generates a detectable signal which is a decrease in the rate of the reaction catalyzed by the enzyme.

A "complex" is an assembly of components. A complex may or may not be stable and may be directly or indirectly detected.

A "system," as used herein, includes a device, apparatus or machinery (e.g., automated) for carrying out the methods of the invention.

A "portion" or "region," used interchangeably herein, of a polynucleotide or oligonucleotide is a contiguous sequence of 2 or more bases. In other embodiments, a region or portion is at least about any of 3, 5, 10, 15, 20, 25 contiguous nucleotides.

A region, portion, or sequence which is "adjacent" to another sequence directly abuts that region, portion, or sequence.

"A", "an" and "the", and the like, unless otherwise indicated include plural forms.

"Comprising" means including.

Conditions that "allow" or "permit" an event to occur or conditions that are "suitable" for an event to occur, such as hybridization, primer extension, oligonucleotide ligation and the like, or "suitable" conditions are conditions that do not prevent such events from occurring. Thus, these conditions permit, enhance, facilitate, and/or are conducive to the event. Such conditions, known in the art and described herein, depend upon, for example, the nature of the nucleotide sequence, temperature, and buffer conditions. These conditions also depend on what event is desired, such as hybridization, cleavage, primer extension or ligation.

The term "3'" generally refers to a region or position in a polynucleotide or oligonucleotide 3' (downstream) from another region or position in the same polynucleotide or oligonucleotide.

The term "5'" generally refers to a region or position in a polynucleotide or oligonucleotide 5' (upstream) from another region or position in the same polynucleotide or oligonucleotide.

The term "3'-DNA portion," "3'-DNA region," "3'-RNA portion," and "3'-RNA region," refer to the portion or region of a polynucleotide or oligonucleotide located towards the 3' end of the polynucleotide or oligonucleotide, and may or may not include the 3' most nucleotide(s) or moieties attached to the 3' most nucleotide of the same polynucleotide or oligonucleotide. This term encompasses a region which is 3' (downstream) from another region or position in the same polynucleotide or oligonucleotide (such as a probe). The "3' most nucleotide" (singular form) refers to the 3' last nucleotide of a polynucleotide or oligonucleotide. The 3' most nucleotides (plural form) includes the 3' most nucleotide and can be preferably from about 1 to about 20, more preferably from about 3 to about 18, even more preferably from about 5 to about 15 nucleotides.

The term "5'-DNA portion," "5'-DNA region," "5'-RNA portion," and "5'-RNA region," refer to the portion or region of a polynucleotide or oligonucleotide located towards the 5' end of the polynucleotide or oligonucleotide, and may or may not include the 5' most nucleotide(s) or moieties attached to the 5' most nucleotide of the same polynucleotide or oligonucleotide. This term encompasses a region which is 5' (upstream) from another region or position in the same polynucleotide or oligonucleotide (such as a probe). The "5' most nucleotide" (singular form) refers to the 5' first nucleotide of a polynucleotide or oligonucleotide. The 5' most nucleotides (plural form) includes the 5' most nucleotide and can be preferably from about 1 to about 20, more preferably from about 3 to about 18, even more preferably from about 5 to about 15 nucleotides.

"Affinity," or "binding affinity", as used herein, means a measure of the strength of bonding between two or more moieties; non-limiting examples of such bonding are hydrogen bonding, electrostatic interactions, Van der Waals interactions, and hydrophobic interactions. In particular, "affinity" or "binding affinity," when used in reference to hybridized nucleic acids, refers to hydrogen bonding between at least partly complementary nucleic acids under defined nucleic acid hybridization conditions. A convenient measure of binding affinity is the melting temperature, Tm, which is the temperature at which 50% of said two strands are in the double-stranded or hybridized form, under given hybridization conditions.

Probes and Methods of the Invention

Oligonucleotide Probes of the Invention

The present invention provides detector oligonucleotide probes, which are useful for the detection and/or quantification of a specific polynucleotide sequence.

Probes A, B, and C have various embodiments and configurations, thus the term "Probe A," "Probe B," "Probe C" generally refers to any of these embodiments, including mirror images. Further, discussion of, for example, probe design, methods, using the probes, etc., refer to exemplary probes and are generally applicable to various probe and method embodiments.

The first oligonucleotide probe, referred to herein as probe A (FIG. 1a), generally comprises a 3'-region (3) that is hybridizable to a sequence of the target nucleic acid; a 5'-region that is not hybridizable to the target nucleic acid under reaction conditions in which sequence 3 and sequence 4 (see below for probe B) can hybridize to the target nucleic acid, and a member of an interacting label pair (F in FIG. 1a) that is generally, but not necessarily, attached to the 5'-end (FIG. 1a). Sequence 3 is preferably at least about 60%, more preferably at least about 80%, and most preferably at least about 90% complementary to the sequence of the target nucleic acid to which it is hybridizable.

The second oligonucleotide probe, referred to herein as probe B (FIG. 1b), generally comprises a 5'-region (4), which is hybridizable to a sequence of the target nucleic acid and a 3'-region (2), which is not hybridizable to the target nucleic acid under reaction conditions in which sequence 3 and sequence 4 can hybridize to the target nucleic acid. Sequence 4 is preferably at least about 60%, more preferably at least about 80%, and most preferably at least about 90% complementary to the sequence of the target nucleic acid to which it is hybridizable. Sequence 2 is hybridizable to a sequence of the region of probe A which is not hybridizable to the target nucleic acid under reaction conditions in which sequence 3 and sequence 4 can hybridize to the target nucleic acid. Sequence 2 is preferably at least about 70%, more preferably at least about 80%, and most preferably at least about 90%, complementary to the sequence of probe A to which it is hybridizable. The length and composition of sequence 2 are designed so that the affinity of the two sequences is too low to allow binding to a significant extent of the two sequences unless probe A and probe B are bound to the same nucleic acid strand of target nucleic acid. The two (mutually hybridizable) sequences of probe A and probe B do not bind to a significant extent when the length and composition of the two sequences are selected according to thermodynamic considerations so as to allow the two probes, when not bound to a target nucleic acid and at a selected incubation temperature, to bind to each other in preferably less than about 5%, more preferably less than about 0.01%, and most preferably less than about 0.0001% of events of contact between the two probes. The appropriate thermodynamic considerations are evident to one skilled in the art, and can be determined empirically and using commonly available tools for calculation of hybridization efficiencies of various nucleic acid sequences.

The target polynucleotide sequences which are complementary to sequence 3 and sequence 4 of probe A and probe B, respectively, are in close proximity (i.e., preferably less than about 10 nucleotides apart, more preferably less than about 7 nucleotides apart, even more preferably less than about 3 nucleotides apart, and generally most preferably contiguous) to each other on the same strand of said target nucleic acid sequence.

In some embodiments, in which a nucleotide polymerase is used, probe B may or may not contain a region which overlaps and may displace or block a sequence on probe C. Accordingly, when using the method of the invention in the presence of a nucleotide polymerase, such as DNA polymerase, and components required for nucleic acid polymerization (nucleoside triphosphates and proper buffer and temperature conditions), there is generally no requirement for homology between the 3' end of probe B and the 5' end of probe C, since displacement is carried out by the extension of the hybridized probe B along the 5' portion of probe A by the polymerase. I.e., there need be little or no overlap between section 1' and section 2' of probe A and hence little or no overlap of binding of probe B and probe C to probe A. In this embodiment, because displacement is accomplished mostly or entirely by extension of probe B to displace or block probe C, the portion of probe B that hybridizes to probe A may be of lower affinity with probe A than in embodiments where probe B displaces probe C without extension. In some embodiments, probe B need not overlap with probe A. In these embodiments, the probes should be designed to allow template switch, e.g., by incorporation of a template switch oligonucleotide (TSO). Such a template switch oligonucleotide has been described in, e.g., U.S. Pat. No. 6,251,639, and references therein (Kurn), and U.S. Pat. Nos. 5,679,512; 5,683,879; and 6,030,774 (Laney et al.).

Figure 2:
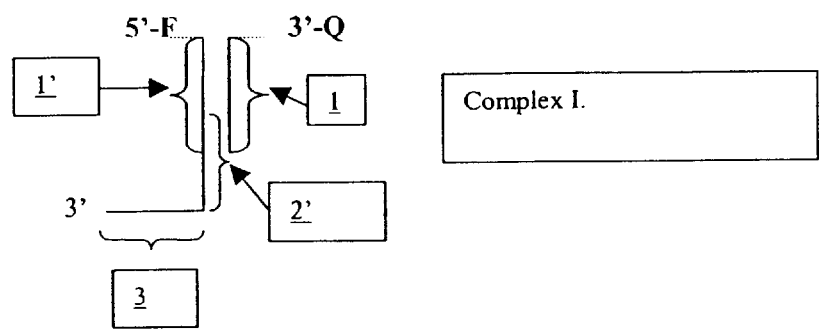
FIG. 2 is a schematic representation of the hybrid complex of probe A and probe C ("Complex I").
Figure 3:
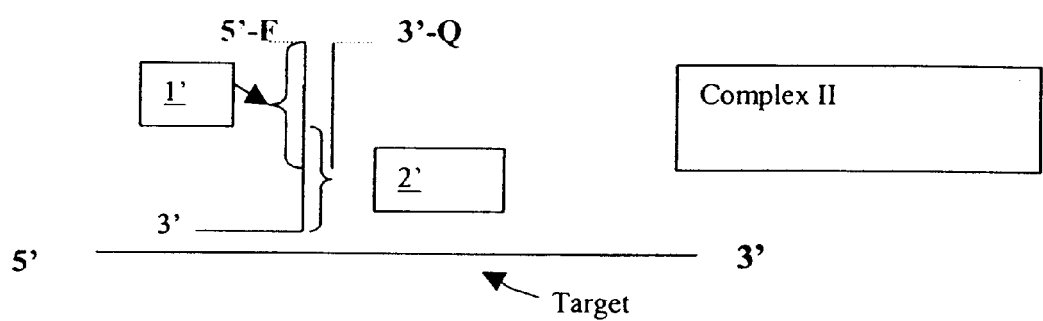
FIG. 3 is a schematic representation of the hybrid complex of probe A, probe C and target nucleic acid ("Complex II").

The third oligonucleotide probe, referred to herein as probe C (FIG. 1c), comprises sequence 1, which is preferably not hybridizable to the target nucleic acid under reaction conditions in which sequence 3 and sequence 4 can hybridize to the target nucleic acid, and is hybridizable to a sequence in the 5'-region of probe A, and a member of an interacting label pair (Q in FIG. 1c) that is generally but not necessarily attached to its 3'-end. Sequence 1 is preferably at least about 60%, more preferably at least about 80%, and most preferably at least about 90% complementary to the sequence in the 5' region of probe A to which it is hybridizable. The affinity of probe A to probe C is high enough to permit binding of the two probes by hybridization of the mutually hybridizable (generally, complementary) sequences, when the two probes are in the same solution and probe A is either free or bound to said target nucleic acid sequence (complex I and complex II, respectively, see FIGS. 2 and 3). As illustrated in FIGS. 2 and 3, moieties (labels) F and Q are in close spatial proximity when the two probes are hybridized.

Interacting Label Pairs.

Probes A and C each comprises a member of an interacting label pair. The members interact when in close proximity, such that separation, or dissociation, of the members on the two probes results in generation of a signal. By "signal" is meant a measurable characteristic. The signal may increase or decrease upon dissociation of the members of the interacting label pair. For example, if the interacting label pair comprises a fluorophore and a quencher, dissociation of the members of the pair generates a detectable signal due to an increase in light energy emitted by the fluorophore in response to illumination. Or, for example, if the interacting label pair comprises subunits of an enzyme, dissociation of the members of the pair generates a detectable signal which is a decrease in the rate of the reaction catalyzed by the enzyme. Each member of the interacting pair may comprise one or more than one molecule or structure. The change in signal may be all-or-none (for example, if the moieties are an enzyme-inhibitor pair, where the enzyme is either active or inactive) or vary over a range (for example, if the moieties are a fluorophore-quencher pair). The change is characteristic for the moieties (labels) employed. In some embodiments, two or more kinds of interacting label pairs may be used in a single sample in order to differentiate, e.g., different target nucleic acid sequences. The detectable signal may be, e.g., a characteristic light signal that results from stimulating at least one member of a fluorescence resonance energy transfer (FRET) pair. Another example of a detectable signal is a color change that results from the action of an enzyme/suppressor pair or an enzyme/cofactor pair on a substrate to form a detectable product. In some embodiments, the signal is a reduction or absence in detectable signal.

Various combinations of moieties (labels) which are capable of producing a detectable signal which differs depending on their degree of proximity, can be used. Any combination or number of moieties (labels) which interact so as to produce a measurable change upon change in the proximity of the moieties (labels) is sufficient; hence, more than one pair of moieties (labels) may be used. Nor is it required that there be a one-to-one correspondence between members of an interacting label pair, especially where one member can affect, or be affected by, more than one molecule of the other member.

Interacting label pairs useful in the present invention are known in the art, see, e.g., U.S. Pat. No. 5,688,648 (Mathies et. al); U.S. Pat. Nos. 5,340,716; 3,999,345; 4,174,384; and 4,261,968 (Ullman et al.); U.S. Pat. Nos. 4,996,143 and 5,565,322 (Heller et al.); U.S. Pat. No. 5,709,994 (Pease et al.); and U.S. Pat. No. 5,925,517 (Tyagi et al.). Examples of suitable moieties (labels) in which one member quenches another include a fluorescent label, a radioluminescent label, a chemiluminescent label, a bioluminescent label, an electrochemiluminescent label, and an enzyme-inhibitor combination. In some embodiments, the interacting moieties (labels) produce little or no signal when in close proximity, and a greater signal when separated. In other embodiments, the interacting moieties (labels) may generate a signal when in close proximity and generate less or no signal when separated. Examples of the latter such moieties (labels) are an enzyme and its cofactor and fragments or subunits of enzymes that must be close to each other for the enzyme to be active.

Various combinations of dye moieties (labels), which are capable of energy transfer when in close spatial proximity, can also be used. For example, interacting moieties (labels) (illustrated in the Figures as F and Q) may be a donor-acceptor dye pair, capable of energy transfer when in close spatial proximity. Label F may be a fluorescent dye and label Q a quencher which is able to absorb the fluorescence signal of label F by an energy transfer mechanism. Alternatively, the moieties (labels) may be ligands for reporter molecules which can interact with each other when brought in close spatial proximity, the interaction of which prevents or enables activity of one of the reporter molecules. Examples for suitable combinations of reporter groups useful for the methods of the invention are enzyme-inhibitor combination, reporter molecules which when reacting with one another form an active enzyme molecule, and the like. The dissociation of the two interacting reporter groups is detectable and indicative of the presence of one or more target nucleic acid sequence(s) in a sample, the quantity of nucleic acid target(s) in a sample or the degree of identity of the sequence of nucleic acid target(s) to that of a reference nucleic acid sequence(s).

Either probe A, or probe C, or both, may optionally incorporate more than one moiety to make up its member of the interacting label pair. The moieties may be located anywhere on the probes as long as they are capable of interacting when probe A and probe C bind together. The moieties may be attached to one end of the probe, or may be attached to the interior of the probe. In some embodiments, a moiety is located at least 1, at least 3, at least 5, or at least 7 nucleotides away from the 3' end probe A and/or the 5' end of probe C (or vice versa for the mirror image probes).

Members of the interacting label pairs may be attached to oligonucleotide probes either during or post-synthesis of the probes. The attachment of a member of an interacting label pair to the rest of the probe is preferably covalent, and means of attachment will vary depending on the probe and the member of the interacting label pair, such means being readily apparent to one of skill in the art.

Oligonucleotide Probes.

Labeled or unlabeled oligonucleotide probes are available commercially, and are usually prepared according to any one of a variety of methods known to those skilled in the art. An oligonucleotide can be prepared by any suitable method, including, for example, cloning and isolation of appropriate sequences using restriction enzymes and direct chemical synthesis by a method such as the phosphotriester method of Narang et al., Meth. Enzymol. (1979), 68:90–99; the phosphodiester method of Brown et al., Meth. Enzymol. 1979, 68:109–151; the diethylphosphoramidite method of Beaucage et al., Tetrahedron Lett. 1981, 22:1859–1862; and the solid support method of U.S. Pat. No. 4,458,066. Methods for synthesizing labeled oligonucleotides are described in, for example, Agrawal and Zamecnik, Nucl. Acids. Res. (1990), 18(18):5419–5423; MacMillan and Vetdine, J. Org. Chem. (1990), 55:5931–5933; Pieles et al., Nucl. Acids. Res. (1989), 17(22):8967–8978; Roger et al., Nucl. Acids. Res. (1989), 17(19):7643–7651; Fisher and Watson, U.S. Pat. No. 5,491,063; and Tesler et al., J. Am. Chem. Soc. (1989), 111:6966–6976. A review of synthesis methods is provided in, for example, Goodchild, Bioconjugate Chemistry (1990), 1(3):165–187.

In some embodiments, the displacement or blocking of probe C from its association with probe A in complex III by probe B (see FIGS. 4 and 5) is a consequence of the higher association affinity of sequence 2 of probe B (see Figure 1b) to its hybridizable sequence, 2', on probe A, when probe B is hybridized to target nucleic acid. The association of sequence 2 with its hybridizable sequence in probe A in complex III is thermodynamically favored insofar as this interaction is uni-molecular when probe B is hybridized to the target nucleic acid. Binding of free probe C to complex IV follows bimolecular reaction kinetics which is less favorable than the unimolecular interaction of probe A and probe B when said probes are bound to the same strand of said target nucleic acid sequence. In the absence of target nucleic acid sequence, probe A generally binds probe C and does not bind probe B. Thus in the absence of target nucleic acid sequence, probe A is generally associated with probe C to form complex I, where interacting label pair member F and interacting label pair member Q are in close spatial proximity (see FIG. 2). Displacement of the portion of sequence 1 of probe C with respect to which sequence 2 has a significant degree of sequence identity from binding to probe A by sequence 2, is sufficient to cause the dissociation of probe C from probe A, leading to the dissociation of interacting label pair, or, alternatively, binding of probe A and probe B to the target nucleic acid sequence and subsequent interaction of sequences 2 and 2' blocks binding of probe C to probe A, thus maintaining the spatial separation of the labels probe A and probe C, whereby a detectable and/or quantifiable signal is generated. Moreover, the close spatial proximity of interacting label pair member F and interacting label pair member Q is maintained following association of complex I with target to form complex II, unless probe B is bound to the same target molecule to form complex III. Complex II is not detectable.

In some embodiments a portion of sequence 2 has a significant degree of sequence identity with respect to a portion of sequence 1 (see FIG. 1c) of probe C. Said significant degree of sequence identity is a sequence identity between the two portions that is at least about 60%, more preferably at least about 75%, more preferably at least about 90%, and most preferably at least about 95%. The percentage of the sequence 1 of probe C which has a significant degree of sequence identity with sequence 2 of probe B required for probe B to be able to displace probe A will depend on thermodynamic considerations for the formation of Complex II and Complex IV. Probes are preferably constructed so that, under the conditions of the reaction, probe C, the 3' region of probe B, and the 5' region of probe A are not substantially hybridizable to the target nucleic acid sequence.

One factor in designing and constructing probes is the free energy parameters of hybridization of given sequences under a given set of hybridization conditions. The free energy parameters for the formation of a given hybrid may be calculated by methods known in the art (see, e.g., Tinoco et al., 1973, Improved Estimation of Secondary Structure in Ribonucleic Acids, Nature, 246, 40–41. and Freier et al., 1986, Improved free-energy parameters for predictions of RNA duplex stability, Proc. Natl. Acad. Sci. U.S.A., 83, 9373–9377; computer programs, e.g., Oligo Primer Analysis Software from Molecular Biology Insight, and references therein), and it is possible to predict, for a given target nucleic acid sequence, probe sequences for which the required free energy changes for formation of various complexes will be met. The type of nucleotides comprising probes A, B, and/or C may also contribute to adjusting or modifying the relative affinities of probes B and C for probe A. For example, the various probes may comprise RNA or peptide nucleic acid (PNA), which may have different affinities for single-stranded DNA than does DNA. Hence, probes may comprise any combination of nucleotide types. Thus, for example, in one aspect, probes A, B, and/or C may comprise RNA, in another aspect, probes A, B, and/or C may comprise DNA and RNA, in another aspect, probes A, B, and/or C may comprise PNA, in another aspect, probes A, B, and/or C may comprise DNA and PNA, in another aspect, probes A, B, and/or C may comprise RNA, and PNA, and in yet another aspect, probes A, B, and/or C may comprise RNA, PNA, and DNA.

One of skill in the art will understand that other factors affect nucleic acid hybridization affinities. For example, any and all of the guanosine-cytosine content of the probe-target and probe—probe duplexes, minor groove binders, O-methylation or other modification of nucleotides, temperature, and salt are potentially important factors in constructing probes with the requisite differences in binding energies. In addition, in some embodiments a nucleotide polymerase, for example, a DNA polymerase, is employed to extend probe B (see below), and in these embodiments the polymerase acts as a "clamp" to further enhance binding of probe B to probe A. Yet another factor affecting affinity is the proximity of probe A to probe B on the target nucleic acid, with the degree of separation of the two probes determining to some extent the degree of interaction; for example, in some cases separation by one nucleotide may be preferable to having the two probes be contiguous. The factors that determine the optimal separation, and other relevant factors, are readily apparent to those of skill in the art, and may be determined empirically. In some embodiments the probes (if hybridized to target nucleic acid sequence) are any of at least 1, at least 2, at least 3, at least 5, at least 7, at least 10, at least 15, at least 20 nucleotides apart. In other embodiments, the probes (if hybridized to target nucleic acid sequence) are any of contiguous, fewer than 1, 2, 3, 5, 7, 10, 15, 20 nucleotides apart.

The hybridization conditions chosen depend on a variety of factors known in the art, for example the length and type (e.g., RNA, DNA, PNA) of probe and target nucleic acids. General parameters for specific (i.e., stringent) hybridization conditions for nucleic acids are described in Sambrook (1989), supra, and in Ausubel (1987), supra. Useful hybridization conditions are also provided in, e.g., Tijessen, 1993, Hybridization With Nucleic Acid Probes, Elsevier Science Publishers B.V. and Kricka, 1992, Nonisotopic DNA Probe Techniques, Academic Press San Diego, Calif. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Increased stringency is achieved by any one or more of the following: elevating the temperature, increasing the ratio of cosolvents, lowering the salt concentration, and the like.

In some embodiments of the invention, the displacement of probe C from probe A by hybridization of probe B to the same target strand (as in complex III) can be further accomplished by extension of probe B along the 5'-portion of probe A by a by a nucleotide polymerase, preferably a DNA polymerase. A "nucleotide polymerase" is a catalyst, usually an enzyme, for forming an extension of a polynucleotide along a DNA or RNA template where the extension is complementary thereto. The nucleotide polymerase is a template dependent polynucleotide polymerase and utilizes nucleoside triphosphates as building blocks for extending the 3'-end of a polynucleotide to provide a sequence complementary with the polynucleotide template. Usually, the catalysts are enzymes, such as DNA polymerases, for example, prokaryotic DNA polymerase (I, II, or III), T4 DNA polymerase, T7 DNA polymerase, Klenow fragment, reverse transcriptase, Vent DNA polymerase, Pfu DNA polymerase, Taq DNA polymerase, and the like, derived from any source such as cells, bacteria, such as *E. coli,* plants, animals, virus, thermophilic bacteria, and so forth. RNA polymerases include T7 RNA polymerase, AMV polymerase, Q-beta-replicase, and so forth. The use of a nucleotide polymerase is particularly useful in cases where the method of the invention is employed for the homogeneous, i.e., simultaneous amplification, detection, and quantification of a target nucleic acid sequence. Isothermal linear amplification, or any other amplification method employing a nucleotide polymerase such as DNA polymerase, is suitable for this aspect of the present invention. This aspect of the invention can be added to other embodiments. Once probe B and probe A are hybridized to the same target strand, the 3'-end of probe B can be extended by the polymerase used in the amplification, and displace and/or block probe C (see FIG. 13). The use of polymerase with strand displacement activity is preferred. When using a method of the invention in the presence of a nucleotide polymerase, such as DNA polymerase, and components required for nucleic acid polymerization (nucleoside triphosphates and proper buffer and temperature conditions), there is generally no requirement for homology between the 3' end of probe B and the 5' end of probe C, since displacement or blocking is carried out by the extension of the hybridized probe B along the 5' portion of probe A by the polymerase. That is, there need be little or no overlap between section 1' and section 2' of probe A and hence little or no overlap of binding of probe B and probe C to probe A. In this embodiment, because displacement and/or blocking is accomplished mostly or entirely by extension of probe B to displace and/or block probe C, the portion of probe B that hybridizes to probe A may be of lower affinity with probe A than in embodiments where probe B displaces probe C without extension. In some embodiments, probe B need not overlap with probe A. In these embodiments, probes should be designed to allow template switch, e.g., a template switch oligonucleotide (TSO) may be incorporated. Such a template switch oligonucleotide has been described in, e.g., U.S. Pat. No. 6,251,639, and references therein (Kurn), and in Patel et al., Proc. Nat'l. Acad. Sci. USA, 1996, 93:2969–2974.

In some embodiments, the mirror image design of the detection probes are provided, as depicted in FIGS. 5*a*, 5*b*, 5*c*, 6, 7 and 8. The mirror image design of a detection probe is expected to only change the probe's polarity. The ability to utilize either one of these designs provides an advantage of choice of probes in cases where sequences 3 or 4 of either probe A or probe B, respectively, in combination with the sequences (in the respective probe) that are not hybridizable to the target nucleic acid under reaction conditions in which sequence 3 and sequence 4 can hybridize to the target nucleic acid, result in internally hybridizable structures leading to secondary structures which are not compatible with the disclosed probe design features. Evaluation of suitable probe sequence can be carried out using tools well known in the art.

Figure 12:
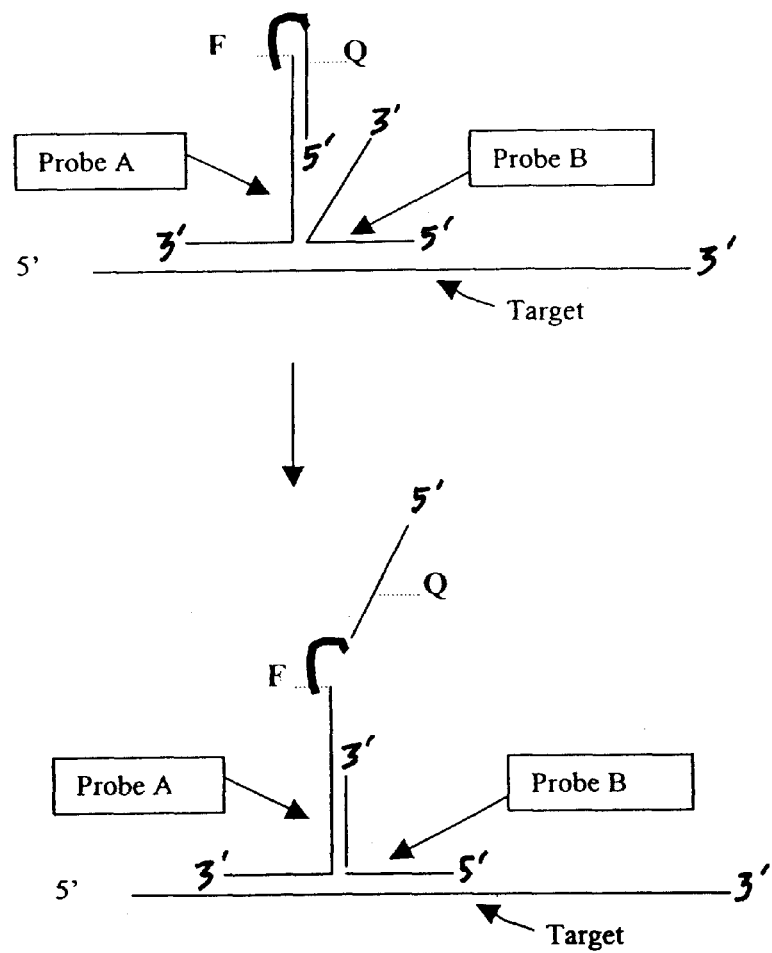
FIG. 12 is a schematic representation of the hybrid complexes formed by a probe B, a single probe that comprises both labels and the functions of both probes A and C, and target nucleic acid.

In some embodiments, a single probe that comprises the functions of probe A and probe C is used. For example, a single probe which comprises two interacting moieties (labels) attached to two sequence portions, respectively, wherein said two sequence portions are hybridizable to each other but, preferably, not to the target nucleic acid under conditions in which the sequences of probe A and probe B that are hybridizable to the target nucleic acid can hybridize to the target nucleic acid, and are capable of forming a hairpin loop structure, as shown in FIG. 12, can be used in the methods of the invention. This design of the detector probe comprises a combination of the two probes each containing a member of an interacting label pair, described above, in the form of a unitary molecule. The two labeled sequence portions of the combination probe may be connected by a nucleotide sequence which is not related to the target sequence, or by a non-nucleotide structure. The two interacting labels are attached to nucleotides of the two hybridizable sequences so that the members of the interacting label pair are placed in close proximity when a hairpin loop structure is formed due to the hybridization of the two mutually hybridizable, sequence portions containing the members of the interacting moiety pair. For example, a hairpin loop is formed when the 5' most sequence of probe A (FIG. 12) is hybridizable to an internal sequence in probe A which is, preferably, not hybridizable to the target. The linker may be peptide, sugar polymer, polyacrylamide, PEG and the like, as will be apparent to those of skill in the art.

Any combination of moieties (labels) described herein may be used in a single probe combining the functions of both probes A and C. The binding of the probe comprising the interacting moieties (labels) (for example, probe A in FIG. 12) and the displacer/blocking probe (for example, probe B in FIG. 12) to the target sequence, to form the tri molecular complex, and the subsequent binding of the displacer/blocking probe (such as probe B as described herein) to its hybridizable sequence on the probe comprising the interacting moieties (labels), results in opening of the hairpin loop structure through the displacement of the 5' end most sequence from hybridization to its internal hybridizable sequence (see, for example, FIG. 12). Alternatively, the displacer/blocking probe (such as probe B as described herein), binds to the target nucleotide sequence and interacts with the first probe while the mutually hybridizable portions of the first probe are not hybridized, thus blocking hybridization. The interacting label pair members are thus separated. The properties of the interacting label pair members (for example, a fluorophore and a quencher) are altered as a result of the separation, and a signal is produced. The detection of the change in spatial proximity of the interacting label pair members provides for detection of the hybridization of the two probes to the target nucleic acid sequence. The signal generated by the hybridization of the two probes indicates the presence of the target sequence and is proportional to the quantity of the target nucleic acid sequence in the test sample.

In another aspect of the invention, compositions are provided which are universal reporter groups and which can be attached to any of a variety of sequences which bind to specific target polynucleotides. These groups differ from the probes previously described in that they do not contain the polynucleotide sequences which are hybridizable to the target nucleic acid sequence (3 and 4 in FIG. 1*a* and 1*b*, respectively), or, in other embodiments, only contain parts of the sequence(s) that bind to target that will be used in the assay. This is based on the fact that, although the parts of probes A and B which interact with target polynucleotide (3 and 4 in FIG. 1) will vary depending on the sequence of the target nucleic acid, the parts of the probes which interact with each other (1, 2, and 1' and 2' in FIG. 1) and which include interacting moieties (labels)(F and Q in FIG. 1) may remain constant or nearly constant even in probes for different target nucleic acids. Hence, in this aspect, the invention provides a first probe which comprises the sections of probe A (as described herein) which interact with probes B and C (sections 1' and 2' in FIG. 1) or portions thereof, and one member of an interacting label pair (F in FIG. 1); a second probe which comprises the section of probe B (as described herein) which hybridizes to probe A (section 2, in FIG. 1) or a portion thereof, but such hybridization is weak unless additional hybridization of an added sequence complementary to the target nucleic acid sequence occurs; and a third probe which is substantially the same as probe C (as described herein), comprising section 1 or a portion thereof (section 1 in FIG. 1c), and a second member of an interacting label pair (Q in FIG. 1). As with the more specific probes which contain the 3 and 4 sections (FIG. 1), the universal probes are designed so that hybridization of the second probe with a section of the first probe is weak unless the second probe also contains a sequence which hybridizes to the target nucleic acid sequence. In the case of the universal probes, this latter sequence must be added to the probe before use, and will vary depending on the nucleic acid sequence to be targeted. These probes have more general characteristics than the previously described probes. They may be attached to any of a variety of sequences which are complementary to different target nucleic acid sequences, and hence provide universal reporter probes which can be combined with unique sequences which bind specific target nucleic acid (e.g., sequence 3 for probe A in FIG. 1 and sequence 4 for probe B in FIG. 1). As with the larger probes, displacement or blocking of probe C by probe B may be accomplished with or without extension.

Methods of Use

The methods generally involve detection and/or quantification of a target nucleic acid sequence (including determining whether a target nucleic acid sequence is present in a sample). The target nucleic acid sequence may be part alone or of an analyte, and in some embodiments may be amplified before detection and/or quantification. Amplification techniques are well-known in the art; see, e.g., U.S. Pat. No. 4,683,202, (Mullis) and U.S. Pat. No. 6,251,639 (Kurn). The target nucleic acid, or one or more of the probes of the invention, may be free in solution, or, in other embodiments, attached to a solid support, e.g., as part of a microarray. Target nucleic acid sequence(s) may be immobilized on a substrate fabricated from a material such as paper, glass, plastic, polypropylene, nylon, polyacrylamide, nitrocellulose, silicon, and optical fiber. Alternatively, the target nucleic acid sequence may be immobilized on the substrate in a two-dimensional configuration or a three-dimensional configuration comprising pins, rods, fibers, tapes, threads, beads, particles, microtiter wells, capillaries, and/or cylinders. In some cases, the target nucleic acid sequence may be attached as a tag to another analyte moiety, e.g., an antibody, the presence, location, or quantity of which is desired to be known. Other examples of possible target nucleic acid sequences will be readily apparent to those of skill in the art. Target nucleic acid sequences for use in the methods of this invention can come from any sources, for example, biological samples, and may be purified and prepared for the methods of the invention using any number of methods, as is well-known in the art. Methods of rendering a double-stranded polynucleotide single-stranded, such as using heat, are known in the art.

Generally, methods of the invention comprise contacting a target nucleic acid with probe A, probe B, and probe C, as described herein, wherein binding of probes A and B to the target nucleic acid, and to each other, leads to displacement of bound probe C from probe A, thus separating interacting moieties (labels) on probe A and on probe C, resulting in a detectable signal, or, alternatively, binding of probe A and probe B to the target nucleic acid sequence blocks binding of probe C, thus maintaining the spatial separation of the labels of probe A and probe C, whereby a detectable and/or quantifiable signal is generated. In some cases, e.g., mutation detection, a decrease in, or lack of, binding of probes A and B to the target nucleic acid sequence indicates the presence of the alteration of interest, e.g., a mutation. This decrease or lack may be detected by comparison with a reference nucleic acid sequence.

Figure 4:
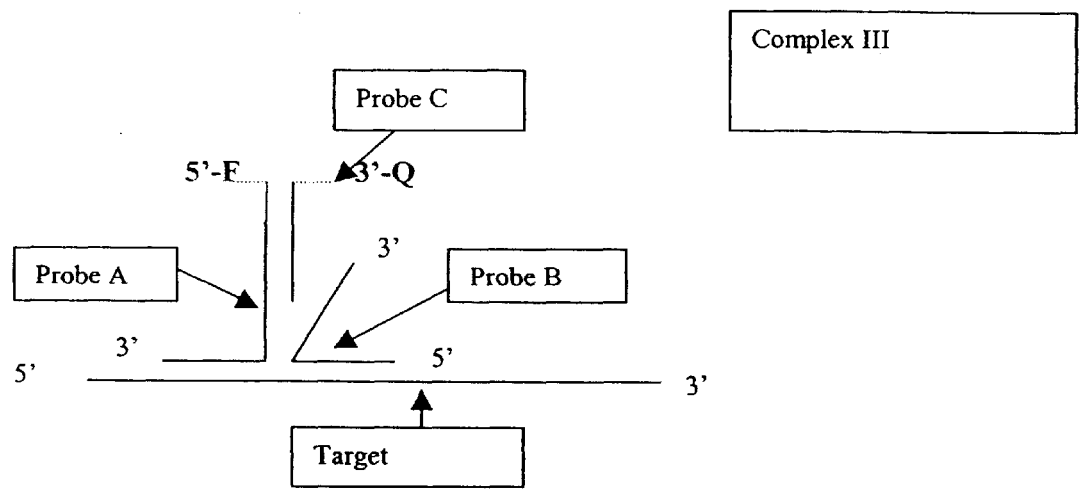
FIG. 4 is a schematic representation of the hybrid complex of probe A, probe B, probe C and target nucleic acid ("Complex III").
Figure 5:
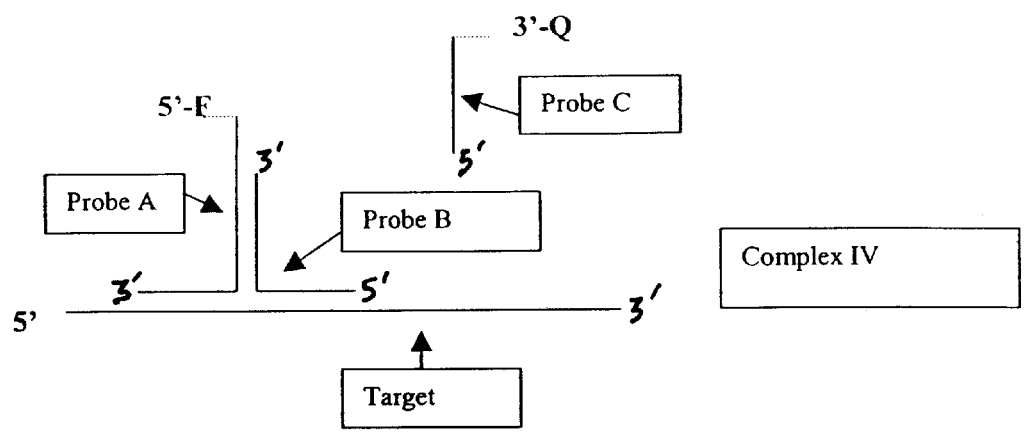
FIG. 5 is a schematic representation of the hybrid complex of probe A, probe B, and target nucleic acid, with a displaced probe C.
Figure 7:
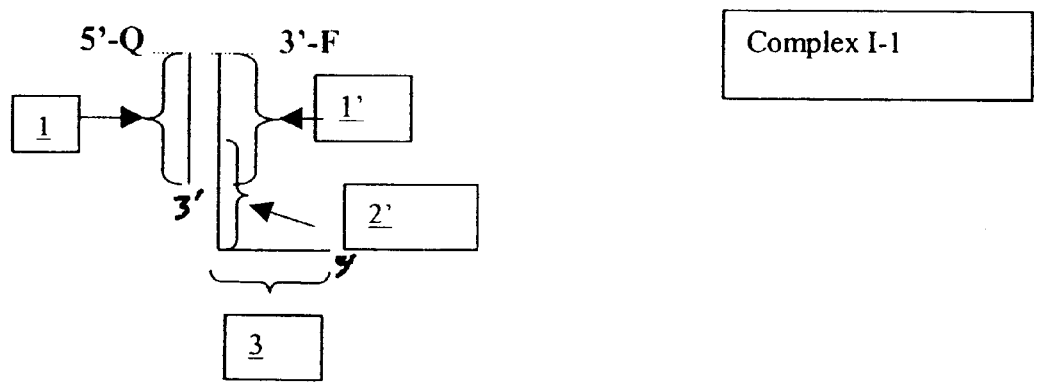
FIGS. 7–10 are schematic representations of the hybrid complexes formed by the mirror image design probes depicted in FIG. 6.
Figure 8:
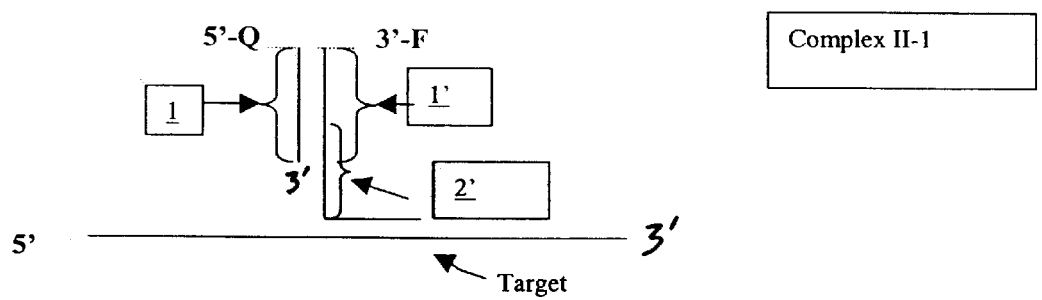
Figure 9:
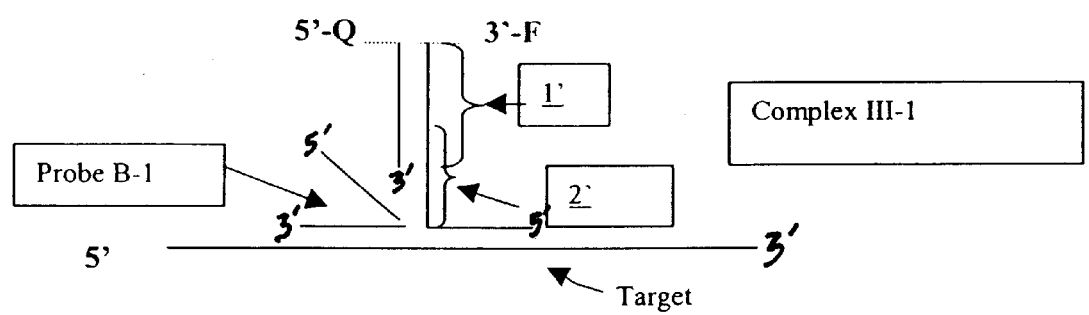
Figure 10:
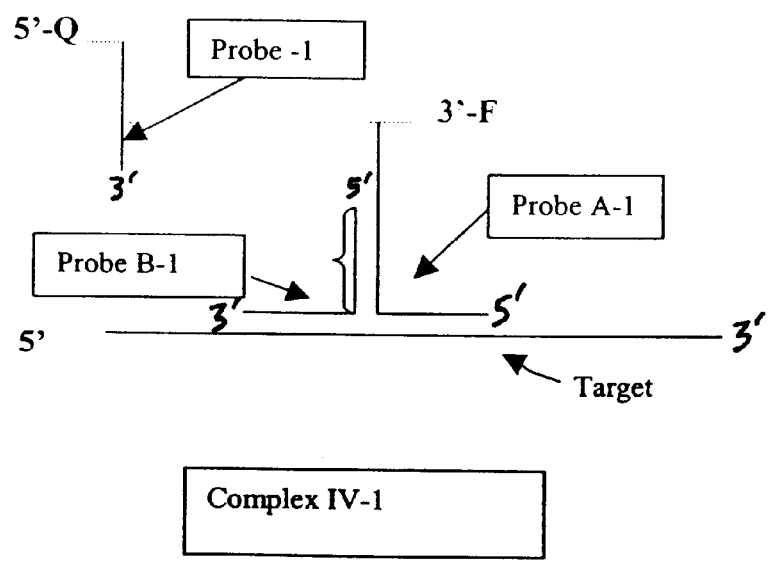

In one embodiment of the invention, detection of a target nucleic acid sequence comprises a) combining a sample suspected of containing said target nucleic acid sequence with probe A, probe B and probe C, for example, provided as a mixture; optionally b) treating the mixture to render the target nucleic acid single stranded (if not already single stranded); and c) incubating the mixture under conditions which are suitable for binding of complex I and probe B to said single stranded nucleic acid target, to form complex III (FIG. 4). In this embodiment, sequence 2 of probe B will lead to displacement or blocking of probe C from its association with probe A to form complex IV, thus increasing the distance between members of an interacting label pair (illustrated in the Figures as F and Q) so as to reduce or eliminate the interaction between the two members of the interacting label pair (FIG. 5).

The dissociation of the moieties (labels) may produce an all-or-none signal (e.g., dissociation of an enzyme-inhibitor pair) or may produce a change in signal characteristic over a range (e.g., fluorescence quenching). The dissociation of the moieties (labels) is detectable and the signal generated is related to the presence of said target nucleic acid. In one embodiment, Probe B is designed to bind to said target at a sequence which is proximal to (i.e., at most about 10 nucleotides apart, or at most about 7 nucleotides apart, or at most about 3 nucleotides apart, or at most about 2 nucleotides apart, or at most about 1 nucleotide apart, or contiguous) to the sequence which is bound by probe A.

In another embodiment of the invention, the 3'-end of the displacer/blocker probe (for example, probe B as described herein), when hybridized to the target sequence and the labeled probe, can be extended by a nucleotide polymerase along a sequence of probe A such that probe C is displaced or blocked from probe A. In this embodiment, probes B and C are both bound to probe A, and there is generally little or no overlap between the binding regions for probes B and C. The extension of the displacer/blocker probe results in displacement or blocking of probe C, which carries one member of an interacting label pair, thus reducing the proximity of the members of the interacting label pair. The change in proximity of the two members of the interacting label pair is detectable. When one member is a quencher and the other is a fluorescer, the binding of the presence of the target is can be detected by the fluorescence signal of the fluorescer. In this embodiment, there need be no overlap of probe B and probe C on probe A; extension of probe B displaces or blocks probe C. Preferably, a nucleic acid polymerase (for, e.g., DNA or RNA polymers) used for extending probe B possesses strand displacement activity. Methods of extension are known in the art.

The various probes may be added simultaneously to a sample suspected of containing said target nucleic acid sequence, or may be added sequentially, or added separately at various timepoints. Such timepoints are evident to one skilled in the art, and can be determined empirically. As described above, signal generation is dependent on the binding of complex II and probe B to the same target nucleic acid sequence. A mixture of probe A and C may be added first to the sample followed by the addition of probe B. It is preferred that the concentration of probe C is greater than that of probe A to ensure the association of substantially all of probe A with probe C in the absence of target polynucleotide. For example, the molar concentration of C may be at least five-fold that of A, at least ten-fold that of A, at least one-hundred-fold that of A, or at least one-thousand-fold that of A.

Figure 11:
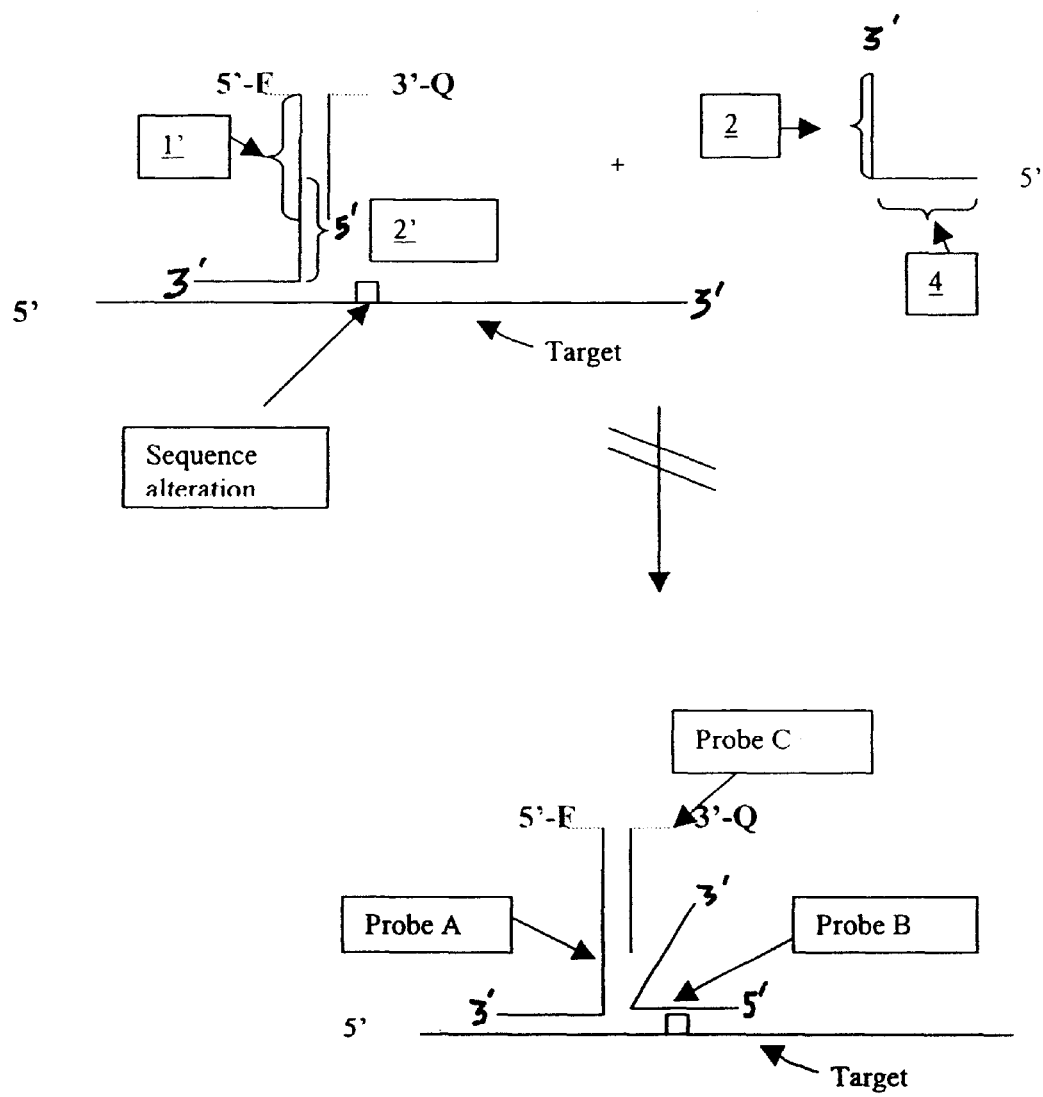
FIG. 11 is a schematic representation of the hybrid complexes formed in the methods of detecting mutation or polymorphism.

The methods of the invention also provide for detection of changes, e.g., mutations, in a defined sequence of the target nucleic acid relative to a reference nucleic acid sequence, where a reference nucleic acid sequence is a known sequence to which others are to be compared, e.g., the wild-type sequence if one is searching for mutations, or the mutated sequence itself. In one embodiment, detection of sequence change, such as mutation or polymorphism, according to the method of the invention, comprises providing a sample containing said target nucleic acid, probe A, probe C and probe B, optionally treating the combination to render the target nucleic acid single stranded (for example, by heating), and further incubating the combination under conditions suitable for formation of a complex III (see FIG. 11). In one embodiment, Probe B is designed to bind to said target at a sequence which is proximal to (i.e., at most about 10 nucleotides apart, or at most about 7 nucleotides apart, or at most about 3 nucleotides apart, or at most about 2 nucleotides apart, or at most about 1 nucleotide apart, or contiguous) to the sequence which is bound by probe A, but only when said sequence of the target nucleic acid which binds to probe B has a degree of sequence identity that is at least about 70%, more preferably at least about 85%, and most preferably at least about 95% that of a reference nucleic acid sequence. Any alteration (relative to a reference nucleic acid sequence) in said sequence of said target nucleic acid results in reduced affinity of probe B to said target nucleic acid sequence and reduces binding of probe B to said target nucleic acid sequence and formation of complex III. The reduction in ability to form complex III reduces displacement or blocking of probe C from complex II and subsequent signal generation. Thus signal generation is related to the degree of sequence identity of said target nucleic acid with respect to a reference nucleic acid sequence. Detection of a variety of mutation types is possible. For example, a mutated sequence can be a point mutation (substitution, deletion, single nucleotide polymorphism) or a mutation involving more than one nucleotide. The properties, e.g., length and type of nucleic acid, of the sequence of probe A, probe B and/or probe C may be adjusted to allow such detection. For example, as will be apparent to one of skill in the art, the shorter the binding section of a probe, the more likely a change in a single nucleotide will alter binding. Other factors which alter binding affinities, including those described supra, will be apparent to one of skill in the art.

Accordingly, in some embodiments, the invention provides methods for genotype determination. The methods are applicable to genotyping of any test organism, including prokaryotic and eukaryotic. The methods of the invention are applicable to the determination of either homozygote or heterozygote genotypes of a diploid organism or cell type. Signal generation, or suppression of signal generation, for a homozygote genotype is generally expected to be up to twice (preferably twice) that of a heterozygote. Various embodiments of genotyping according to methods of the invention are provided.

In one embodiment, allele-specific probe A, and/or probe B, are used. The detection of signal thus indicates the presence of a specific allele. It is possible to use different pairs of interacting moieties (labels), which produce distinguishable signals, for each of the specific alleles, thus providing a method for simultaneous detection of more than one known allele. It is possible to use the methods of the invention for the detection of any sequence alterations in the target sequence which is complementary to the target-specific sequences of probe A and/or probe B. In some embodiments, the target-specific sequence of the probe(s) is designed so that any alteration of the target sequence in this region will adversely affect the hybridization of either one, or both, of the probes to the target, thus preventing or diminishing cooperative binding of the non-target specific sequences of the probe(s) and the subsequent signal generation. The degree of sequence identity between the altered target sequence and unaltered target sequence is preferably less than about 50%, more preferably less than about 10%, even more preferably less than about 5%, and most preferably less than about 1%. In other embodiments, the sequence of the probe(s) is designed to hybridize more preferentially to a suspected altered target sequence than to an unaltered target sequence, so that a detectable signal is generated in the presence of the suspected altered target sequence.

Another embodiment of the invention provides methods of detection and/or quantification of multiple target nucleic acid sequences in a sample. These methods employ two or more sets of each of probe A, probe B and probe C, with each combination of probe A, probe B and probe C being specific for each target nucleic acid sequence. In these methods, two or more kinds of interacting label pairs (i.e., with respect to combinations of interacting label pair members F and Q as illustrated in FIG. 1), each specific for a defined target nucleic acid sequence, are provided. For example, various combinations of dye moieties, which are capable of energy transfer when in close spatial proximity, can be used. Alternatively, the members of the label pair may be ligands for reporter molecules which can interact with each other when brought in close spatial proximity, the interaction of which prevents or enables activity of one of the reporter molecules. Examples for suitable combinations of reporter groups useful for the method of the invention are any of those known in the art and/or described herein, including enzyme-inhibitor combinations, reporter molecules which when reacting with one another form an active enzyme molecule, and the like. The dissociation of the two members of an interacting label pair, and subsequently the dissociation of the two interacting reporter groups, is detectable and indicative of the presence of said target nucleic acid sequence in said sample, the quantity of said nucleic acid target in said sample or the identity of said sequence of said nucleic acid target to that of a reference nucleic acid sequence.

It will be readily apparent that all of the above embodiments are suitable not only for detection but for quantification, using methods apparent to one of skill in the art, e.g., the use of standard quantities of target DNA as references against which to measure an unknown sample. For both detection and quantification, a control lacking the target nucleic acid sequence may be run and compared to the sample run under the same conditions, to determine the presence and/or amount of target nucleic acid sequence in the sample.

The invention may also be used in conjunction with nucleic acid amplification techniques, as exemplified in Example 2. Any method of nucleic acid sequence amplification may be used for the amplification of a target nucleic acid sequence. These methods include PCR (Mullis et al. U.S. Pat. No. 4,582,788), isothermal exponential amplification methods such as nucleic acid sequence-based amplification (U.S. Pat. No. 5,654,142), transcription-mediated amplification (U.S. Pat. No. 5,766,849, or strand-displacement amplification (U.S. Pat. No. 5,648,211), or isothermal linear amplification (U.S. Pat. No. 6,251,639), linked linear amplification (Wallace et al., U.S. Pat. No. 6,027,923), ligation-based amplification (Wu et al., Genomics 4:560, 1989). For a discussion of methods of amplification, see U.S. Pat. No. 6,251,639, and references therein. The detection and quantification of the amplification products may be carried out simultaneously with the amplification reactions, or in a separate step following the amplification reaction. When the detection and quantification of the amplification products are carried out by generation of signals by displacement or blocking of a probe that is labeled with a quencher (probe C) by polymerase catalyzed probe extension, the nucleotide polymerase (e.g., DNA polymerase) employed in the amplification step may be used in the signal generation step. The quantification of amplification products is directly related to the amount of target nucleic acid in the sample. The efficiency of amplification of the target nucleic acid sequence may be separately determined. Control samples with known amounts of the target nucleic acid sequence may be subjected to amplification and quantification by the method of the present invention to produce a standard curve that can be used for the determination of the amount of the test sample. Quantification of a test nucleic acid in a sample may also be carried out by simultaneous amplification and detection of a test nucleic acid sequence and a control nucleic acid sequence that is different than the test sequence and serves as an internal control for quantification.

Compositions and Kits of the Invention

The invention also provides compositions, kits, complexes, reaction mixtures and systems comprising various components (and various combinations of the components) used in the methods described herein.

The compositions may be any component(s) (including any of the probe embodiments and any combination of the various probe embodiments), reaction mixture and/or intermediate described herein, as well as any combination. In one embodiment, the invention provides a composition comprising probe A, a composition comprising probe B, and/or a composition comprising probe C. In other embodiments, various combinations of the probes may be provided in compositions of the invention. For example, the invention may provide a mixture of probes A, B, and C; or it may provide, for example, a mixture of probes A and C, and provide probe B separately. When probes A, B, and C are provided together, probes A and C may form, under suitable reaction conditions, Complex I (see FIG. 2). In the presence of target nucleic acid, all of the complexes of the invention may be present (see FIGS. 2–5), in varying relative amounts, depending on the affinity of the probes for the target nucleic acid and for each other, with concomitant signal generation. When probes A and C are provided together, and probe B is provided separately, under suitable reaction conditions probes A and C may combine to form Complex I (see FIG. 2) or, in the presence of target nucleic acid, Complex II (see FIG. 3). On addition of probe B, said compositions may, in the presence of target nucleic acid, form Complexes III and IV as well (see FIGS. 4 and 5, respectively), as described herein, with concomitant signal generation.

Figure 13:
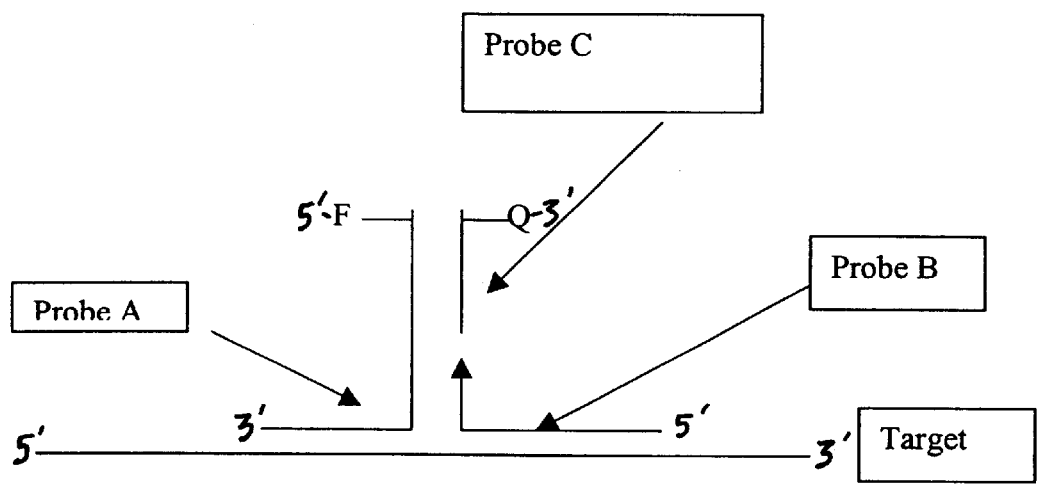
FIG. 13 is a schematic representation of probes of the invention in which displacement of probe C is carried out by extension of probe B along the 5'-portion of probe A by a nucleotide acid polymerase, for example, a DNA polymerase. As an example of an interacting label pair, "F" and "Q" are labels, such as, for example, a fluorophore and a quencher.

In some embodiments, probes B and C may contain portions of their sequences which overlap, each of which is hybridizable to the same portion of probe A, whereas in other embodiments B and C may contain no portions of their sequences which are homologous (see, e.g., FIG. 13). In some embodiments, nucleotide polymerase, for example DNA polymerase, may be provided as a separate component, or as part of a composition. In these embodiments, suitable single nucleoside triphosphates, for example dNTPs may also be provided in order to allow extension of probes of the invention.

In some compositions, a single probe that comprises the functions of probe A and probe C is provided. This probe may be provided by itself, or in combination with probe B. For example, one aspect of the invention may comprise a composition comprising a first probe and a second probe, wherein the first probe comprises a 3' region that is hybridizable to a target polynucleotide comprising a sequence of interest, a 5' region comprising two mutually hybridizable sequences and members of an interacting moiety pair; the second probe comprises a 5' region which is hybridizable to the target polynucleotide, and a 3' region which is not hybridizable to the target polynucleotide and is hybridizable to a sequence in the 5' region of the first probe; wherein hybridization of the second probe to the target polynucleotide is associated with a decrease in extent of hybridization between the mutually hybridizable sequences of the first probe; whereby generation of a detectable signal associated with said decrease in extent of hybridization between the mutually hybridizable sequences indicates presence of the sequence of interest in the sample.

This composition may further comprise components for extension of the 3' end of the second probe along a sequence in the 5' region of the first In the compositions of the invention, interacting label pairs may be provided attached to the suitable probes (i.e., probes A and C as described herein). In other compositions, probes and/or interacting label pairs may be provided separately. Members of interacting label pairs include a fluorescent moiety, a radioluminescent moiety, a chemiluminescent moiety, a bioluminescent moiety, an electrochemiluminescent moiety, and an enzyme-inhibitor combination. In some embodiments, the members of the interacting label pair produce little or no signal when in close proximity, and a greater signal when separated. In other embodiments, the members of the interacting label pair may generate a signal when in close proximity and generate less or no signal when separated. Examples of the latter such interacting label pairs are an enzyme and its cofactor and fragments or subunits of enzymes that must be close to each other for the enzyme to be active. In the latter case, suitable reagents for attachment of the members of the interacting label pair to the appropriate probes and locations, may also be provided. Such reagents will be readily apparent to one of skill in the art.

In all compositions, probes A, B, and/or C may be designed to bind to specific nucleic acid sequences, or they may be the universal probes described above, which lack the sequences which bind to target nucleic acid sequence. Alternatively, the probes may contain part of a sequence which binds to the target nucleic acid. The remainder of the binding sequence of the probe(s) may be provided by the user in order to match the target sequence or sequences to be detected and/or quantified. Probe C, especially, is amenable to provision as a composition which is universal or nearly universal, since probe C does not contain sequences which bind to the target nucleic acid, and therefore the sequence of probe C is not substantially dependent on the sequence of the particular target nucleic acid to be detected. Suitable reagents and compounds to accomplish attachment of probe sequences to sequences which bind to target nucleic acid sequences, and/or extension of probe sequences to comprise sequences which bind to target nucleic acid sequences, may also be provided.

In other embodiments, the invention provides compositions further comprising reference nucleic acid for detection and/or quantification of changes in nucleic acid. A composition may provide probe A, probe B, and/or probe C, in combination with or separate from a reference nucleic acid sequence. For example, a composition may provide probes A and C, and reference nucleic acid. Under suitable reaction conditions, probes A and C may form Complex II (see FIG. 3) with the reference nucleic acid. Addition of probe B to the mixture may result in generation of a detectable signal, which may be compared to the signal generated by addition of probes A, B, and C to the target nucleic acid sequence under similar reaction conditions.

In yet other embodiments, probes of the composition may target more than one target nucleic acid. For example, a composition may contain more than one probe A, each of which targets a different nucleic acid sequence. A composition may further contain more than one probe B, each of which targets a different nucleic acid sequence. Probe C may be the same or it may be different for the various probes A and/or B provided. These compositions are useful in, for example, determining the presence or absence and/or quantity of more than one target nucleic acid sequence at a time, in determining the presence or absence and/or quantity of various alleles, or in determining the presence or absence or quantities of various polymorphisms or mutations in a sequence.

All compositions described herein may also comprise the mirror image probes depicted, for example, in FIGS. 6 through 10.

The compositions are generally in a suitable medium, although they can be in lyophilized form. Suitable media include, but are not limited to, aqueous media (such as pure water or buffers).

In some embodiments, the invention provides compositions comprising any of the complexes (which are generally considered as intermediates with respect to the final products) described herein (see also the figures for exemplary schematic depictions of these various complexes). Complexes are schematically depicted in FIGS. 2–10, and in FIG. 13. As an example, one complex of the invention is a complex comprising: (a) probe A; and (b) probe C, wherein probe C is bound to probe A to from Complex I, as shown in FIG. 2. Probe A may comprise a nucleic acid sequence that binds to target nucleic acid. Alternatively, probe A may comprise none or only part of a nucleic acid sequence which binds to target nucleic acid. If probe A comprises a nucleic acid sequence which binds to target nucleic acid, the complex may further comprise a nucleic acid which binds to probe A where target nucleic acid may bind, e.g., a reference nucleic acid. The complex, with or without a nucleic acid which binds to probe A, may also comprise probe B.

The invention also provides kits for conducting the methods described herein. These kits, in suitable packaging and generally (but not necessarily) containing suitable instructions, contain one or more components used in the detection and/or quantification methods, including mirror-image components. The kits may be used for any one or more of the uses described herein, and, accordingly, may contain instructions for any one or more of the following uses: determining whether a target nucleic acid sequence is present in a sample, detecting a target nucleic acid sequence, quantifying a target nucleic acid sequence, comparing target nucleic acid sequence to reference sequence(s), determining genotype, determining allele composition of target nucleic acid(s), detecting and/or quantifying multiple nucleic acid sequences, and use of the methods in conjunction with nucleic acid amplification techniques.

The kits of the invention comprise one or more containers comprising any combination of the components/reagents (e.g., probes) described herein, and the following are examples of such kits. A kit for detecting a target nucleic acid sequence may contain probe A, probe B, probe C, and optionally components for extension of probe B, if used. A kit for quantifying a nucleic acid sequence may further comprise a reference or set of references of known quantity, to which the target nucleic acid may be compared. A kit for comparing a target nucleic acid sequence with reference sequence(s) may further comprise said reference sequence(s). A kit for determining genotype and/or allele composition may further comprise a reference sequence corresponding to one of the alleles to be determined, or more than one reference corresponding to more than one allele. A kit for detecting and/or quantifying a multiple nucleic acid sequences may contain one or more sets of probe A, probe B, and/or probe C, each for a given target nucleic acid sequence, as well as optionally comprising a reference or set of references for one or more of the target sequences. Kits may also optionally include any of one or more of the enzymes described herein, substrates for enzymes (for example, when an enzyme is used a member of an interacting label pair) as well as deoxynucleoside triphosphates and/or ribonucleoside triphosphates. Kits may also include one or more suitable buffers (as described herein). One or more reagents in the kit can be provided as a dry powder, usually lyophilized, including excipients, which on dissolution will provide for a reagent solution having the appropriate concentrations for performing any of the methods described herein. Each component can be packaged in separate containers or some components can be combined in one container where cross-reactivity and shelf life permit.

The kits of the invention may optionally include a set of instructions, generally written instructions, although electronic storage media (e.g., magnetic diskette or optical disk) containing instructions are also acceptable, relating to the use of components of the methods of the present invention for the intended nucleic acid detection and/or quantification, and/or, as appropriate, for using the detection and quantification methods in conjunction with amplification techniques. The instructions included with the kit generally include information as to reagents (whether included or not in the kit) necessary for practicing the methods of the presentation invention, instructions on how to use the kit, and/or appropriate reaction conditions.

In another embodiment, the invention provides a kit for the detection or quantification of a target polynucleotide, comprising a first probe and a second probe, wherein the first probe comprises a 3' region that is hybridizable to a target polynucleotide comprising a sequence of interest, a 5' region comprising two mutually hybridizable sequences and members of an interacting moiety pair; the second probe comprises a 5' region which is hybridizable to the target polynucleotide, and a 3' region which is not hybridizable to the target polynucleotide and is hybridizable to a sequence in the 5' region of the first probe; wherein hybridization of the second probe to the target polynucleotide is associated with a decrease in extent of hybridization between the mutually hybridizable sequences of the first probe; whereby generation of a detectable signal associated with said decrease in extent of hybridization between the mutually hybridizable sequences indicates presence of the sequence of interest in the sample. This kit may further comprise a reference polynucleotide to which the target polynucleotide may be compared instructions for use of the kit to detect or quantify the target polynucleotide, and/or a nucleic acid polymerase with strand displacement activity.

The component(s) of the kits of the invention may be packaged in any convenient, appropriate packaging. The components may be packaged separately, or in one or multiple combinations. The relative amounts of the various components in the kits can be varied widely to provide for concentrations of the reagents that substantially optimize the reactions that need to occur to practice the methods disclosed herein and/or to further optimize the sensitivity of any assay. In kits made up of the reagents of the present invention, probe A and probe C (or a unitary probe which combines the sequences of probe A and probe C) may be provided with or without interacting label pairs, and suitable members of an interacting label pair may be attached before assay; this is useful when several different interacting label pairs are to be used, and/or members of the interacting label pair are more subject to degradation than the rest of the probe molecule.

The invention also provides systems for effecting the detection and/or quantification methods described herein. These systems comprise various combinations of the components discussed above. For example, in some embodiments, the invention provides a system suitable for detecting target nucleic acid sequence (or quantifying target polynucleotide sequence) comprising (a) probes A, B, and C (as described herein), and (b) optionally, a polynucleotide polymerase (preferably DNA polymerase) and nucleoside triphosphates for probe extension. In some embodiments, a single probe may combine the functions of probes A and C. In some embodiments, more than one probe of any or each type may be provided in order to target multiple nucleic acid sequences. In some embodiments, the system further comprises reference nucleic acid sequence(s). In some embodiments, the system further comprises a standard or set of standards for quantifying nucleic acids. In some embodiments the system may also comprise interacting label pairs, as described herein, to be attached to probes before use. In some embodiments, the system may comprise components used for attaching a sequence complementary to the target nucleic acid sequence to universal probes which lack some or all of such sequence. In all embodiments, the system may comprise suitable buffers, enzymes, substrates, and/or apparatus and other components necessary to provide the proper reaction conditions for detection and/or quantification of target nucleic acid.

In another aspect, the invention provides reaction mixtures (or compositions comprising reaction mixtures) which contain various combinations of components (e.g., probes) described herein. In some embodiments, the invention provides reaction mixtures comprising (a) probe A, probe B, and probe C, and (b) optionally, a nucleic acid polymerase. Such reaction mixtures may further comprise reference nucleic acid(s). In addition, such reaction mixtures may contain the necessary nucleoside triphosphates for strand extension. In some embodiments, the invention provides reaction mixtures comprising a) a unitary probe combining the functions of probe A and probe C, and probe B, and (b) optionally, a nucleic acid polymerase. Such reaction mixtures may further comprise reference nucleic acid(s). In addition, such reaction mixtures may contain the necessary nucleoside triphosphates for strand extension. In all cases, reaction mixtures may further comprise buffers, enzymes, enzyme substrates, and other components necessary for detection and/or quantification of a target polynucleotide.

In one embodiment, the invention comprises a reaction mixture, comprising a first probe, a second probe and a third probe, wherein the first probe comprises a 3' region that is hybridizable to a target polynucleotide comprising a sequence of interest and a 5' region comprising a first member of an interacting moiety pair; the second probe comprises a 5' region which is hybridizable to the target polynucleotide, and a 3' region which is hybridizable to a sequence in the 5' region of the first probe; the third probe comprises a sequence which is hybridizable to a sequence in the 5' region of the first probe and a second member of the interacting moiety pair; wherein hybridization of the second probe to the target polynucleotide is associated with displacement of a sequence of the third probe from the first probe; whereby generation of a detectable signal associated with displacement of the third probe from the first probe indicates presence of the sequence of interest in the sample; and further comprising a nucleic acid polymerase with strand displacement activity.

In another embodiment, the invention comprises a reaction mixture, comprising a first probe and a second probe, wherein the first probe comprises a 3' region that is hybridizable to a target polynucleotide comprising a sequence of interest, a 5' region comprising two mutually hybridizable sequences and members of an interacting moiety pair the second probe comprises a 5' region which is hybridizable to the target polynucleotide, and a 3' region which is not hybridizable to the target polynucleotide and is hybridizable to a sequence in the 5' region of the first probe; wherein hybridization of the second probe to the target polynucleotide is associated with a decrease in extent of hybridization between the mutually hybridizable sequences of the first probe; whereby generation of a detectable signal associated with said decrease in extent of hybridization between the mutually hybridizable sequences indicates presence of the sequence of interest in the sample; and further comprising a nucleic acid polymerase with strand displacement activity.

The following Examples are provided to illustrate but not limit the present invention.

EXAMPLES

Example 1

Detection of the presence of target nucleic acid sequence
The sequence of the target nucleic acid is as follows:

```
5'-AGATTCAGTG AAGGATAGTG CTGAATTTCC ATCTCTGAGT

TCAAAATAAT TTGAGAAAAT ATGATAGAAA TTGTGAAGTA

CTAGATTTCA GAAAATATGA TTAGAAAAAG CGTGGTACAT

CTTAAAATAT AACTT TCTGG CACTGAATCC TGCCACCTAC

CATCTCCACC TCTAACATGG ATGCAGTTTA TAATTAAGAG

CTTTCAGATT TTGAGCA-3'  (SEQ ID NO:1)
```

The underlined sequence is the sequence complementary to the corresponding (underlined) of probes A and probe B.

```
Probe A
3'-CTTTTATACTAATCTTTTTCGCACC
CATCATCATCATCATCATCATGTAATCGTAATCGAAGAC-FL
(SEQ ID NO:3)

Probe C
5'-GTAGTAGTACATTAGCATTAGCTTCTG-Q (SEQ ID NO:2)

Probe B
3'-ATGATGATGATGTAGAATTTTATATTGTT-5' (SEQ ID NO:4)
```

Probe C is complementary to the 5'-end sequence of probe A. The 3'-most sequence of probe B is complementary to the sequence of probe A which is in the 5'-direction of the non-target complementary sequence (in italics).

In this example the displacement or blocking of probe C from probe A to disrupt quenching of fluorescence of probe F by quencher Q, is carried out by extension of the 3'-end of probe B hybridized to the non target complementary sequence of probe A, when probe A and probe B are hybridized to the same strand of the target nucleic acid, by a DNA polymerase.

Sample suspected of containing the test nucleic acid sequence is combined with a reaction-mixture composed of Probes A, Probe B and Probe C, dNTPs and DNA polymerase in a buffer. The buffer composition is similar to that used primer extension by DNA polymerase. The reaction mixture is heated to 95° C. for 3 min. for denaturation of the target nucleic acid and the mixture is further incubated at 55° C. for 10 min.

If the target nucleic acid sequence is present in the sample, probe A and Probe B will hybridize to the corresponding sequences on the target. Probe C hybridizes to probe A and the labels F and Q are brought to close proximity, which results in quenching of the fluorescence signal of F. Probe C is in large excess over probe A, to ensure binding of more than 99.999% of probe A. Probe A and probe B are present in amount of 1 to 10 pmoles.

Hybridization of probe A and probe B to the same strand of the target nucleic acid enhances the hybridization of the 3'-end of probe B to the corresponding non-target complementary sequence of probe A. DNA polymerase binds to the hybridized 3'-end of probe B and extends it along the 5'-end strand of probe A. The extension of probe B by a DNA polymerase results in the displacement or blocking of probe C from its hybridization to probe A, thus leading to dissociation of Q from F. The presence, and amount of the target nucleic acid is assessed by measuring the fluorescence of the reaction mixture. The fluorescence is measured either at the end of the incubation or in real time during the incubation period. The amount of target is proportional to the measured fluorescence.

Example 2

Detection and Quantification of Target Nucleic Acid Sequence in a Sample Using the Method of the Present Invention for the Detection and Quantification of Products of Amplification Reaction Any method of nucleic acid sequence amplification may be used for the amplification of a target nucleic acid sequence. These methods include PCR, isothermal exponential amplification methods such as NASBA, TMA or SDA, or isothermal linear amplification (U.S. Pat. No. 6,251,639). The detection and quantification of the amplification products may be carried out simultaneously with the amplification reactions, or in a separate step following the amplification reaction. When the detection and quantification of the amplification products are carried out by the method described in example 1, i.e. generation of fluorescent signals by displacement or blocking of a probe that is labeled with a quencher (probe C) by polymerase catalyzed probe extension, the DNA polymerase employed in the amplification step is used in the signal generation step. The conditions for amplification of the target nucleic acid sequence to be detected or quantified are known to those skilled in the art. The quantification of amplification products is directly related to the amount of target nucleic acid in the sample. The efficiency of amplification of the target nucleic acid sequence may be separately determined. Control samples with known amounts of the target nucleic acid sequence may be subjected to amplification and quantification by the method of the present invention to produce a standard curve that can be used for the determination of the amount of the test sample. Quantification of a test nucleic acid in a sample may also be carried out by simultaneous amplification and detection of a test nucleic acid sequence and a control nucleic acid sequence that is different than the test sequence and serves as an internal control for quantification. Thus, the reaction mixture contains a control nucleic acid sequence, the one or more primers required for amplification of the control and test nucleic acid sequences, the probes required for the detection and quantification of the amplification products generated from the test and control nucleic acid sequence, the enzyme required for amplification of the test and control nucleic acid sequences, dNTPs or rNTPs, any accessory proteins, such as single stranded DNA binding protein and the like, and the buffer components. The amplification and detection of amplification products of the test and control nucleic acid sequences are carried out in the same reaction vessel. In the case of PCR amplification, the reaction mixtures are subjected to incubations at varied temperatures, as commonly known in the art. The incubations are carried out in a thermo-cycler. The incubation temperatures are selected for optimal denaturation (80 to 99° C.), annealing of the primers (45° C. to 72° C.) and primer extension (60° C. to 75° C.). The duration and temperature for each of the incubation steps are determined according to the sequence of the test nucleic acid and the selected primers and probes. A commonly used medium for PCR amplification comprises 1 to 5 mM $MgCl_2$, Tris buffer at pH 8.5, and 0 to 50 mM KCl. The reaction is carried out in the presence of 250 nM of each dNTP and 0.1 to 1 uM of each of the primers. The reactions are commonly carried out using Taq DNA polymerase, or other suitable thermostable DNA polymerases such as Pfu, Vent and the like.

Isothermal Single Primer Amplification (SPIA) can be also employed for amplification of the test and/or control nucleic acid and detection and quantification of the amplification products according to the method of the invention. A single composite primer, comprising a 3' DNA portion and a 5' RNA portion, is used for amplification of a defined sequence. Specific primers for the control and test nucleic acid sequences are employed. The reaction is carried out in a buffer similar to that described for the PCR reaction, with 2 to 5 mM $MgCl_2$, 0.25 to 0.5 mM dNTPs, 3 ug T4gp32 (USB) or similar ssDNA binding protein, a DNA polymerase with strong strand displacement activity, such as Bca or Bst polymerases, RNase H, and 1 to 5 mM DTT. The reaction mixtures containing the primers, probes and samples and/or controls, are first denatured by incubation at 95° C. for 2 to 5 min., and the primer(s) are allowed to anneal to the respective target by incubation at 55° C. for 5 min. The enzyme mixture is than added to the reaction tubes and the amplification and signal generation and detection is carried out by further incubation at this temperature for 30 min.

Although the foregoing invention has been described in some detail by way of illustration and example for purposes of clarity of understanding it, it will be apparent to those skilled in the art that certain changes and modifications could be practiced.

What is claimed is:

1. A method of determining whether a target nucleic acid sequence is present in a sample, said method comprising:
contacting said sample with a first probe, a second probe, and a third probe, under conditions allowing hybridization of the first and second probes to the target nucleic acid sequence, if present, and hybridization of the first probe to the third probe, in the absence of the target nucleic acid sequence, and hybridization of the second probe to the first probe when the second probe is hybridized to the target nucleic acid sequence, wherein:
(i) the first probe comprises
(a) a polynucleotide comprising a 3' region which hybridizes to a first region of the target nucleic acid sequence, if present, and
(b) a first member of an interacting label pair;
(ii) the second probe comprises
(a) a polynucleotide comprising a 5' region which hybridizes to a second region of the target nucleic acid sequence, if present, and
(b) a 3' region which hybridizes to a sequence in the 5' region of the first probe, if the target nucleic acid sequence is present; and
(iii) the third probe comprises
(a) a polynucleotide which hybridizes to a sequence in the 5' region of the first probe, and
(b) a second member of an interacting label pair;
wherein when said third probe is hybridized to said first probe, said first and second members of the interacting label pair are brought into proximity and interact;

and wherein, in the presence of the target nucleic acid sequence, said 3' region of said first probe hybridizes to said first region of the target nucleic acid sequence and said 5' region of said second probe hybridizes to said second region of the target nucleic acid sequence and said 3' region of said second probe hybridizes to the first probe, causing dissociation of the first and second members of the interacting label pair;

whereby generation of a detectable signal caused by dissociation of the interacting label pair indicates presence of the target nucleic acid sequence.

2. A method of determining whether a target nucleic acid sequence is present in a sample, said method comprising:

contacting said sample with a first probe, a second probe, and a third probe, under conditions allowing hybridization of the first and second probes to the target nucleic acid sequence, if present, and hybridization of the first probe to the third probe, in the absence of the target nucleic acid sequence, and hybridization of the second probe to the first probe when the second probe is hybridized to the target nucleic acid sequence, wherein:

(i) the first probe comprises
(a) a polynucleotide comprising a 5' region which hybridizes to a first region of the target nucleic acid sequence, if present, and
(b) a first member of an interacting label pair;

(ii) the second probe comprises
(a) a polynucleotide comprising a 3' region which hybridizes to a second region of the target nucleic acid sequence, if present, and
(b) a 5' region which hybridizes to a sequence in the 3' region of the first probe, if the target nucleic acid sequence is present; and (iii) the third probe comprises
(a) a polynucleotide which hybridizes to a sequence in the 3' region of the first probe, and
(b) a second member of an interacting label pair;

wherein when said third probe is hybridized to said first probe, said first and second members of the interacting label pair are brought into proximity and interact;

and wherein, in the presence of the target nucleic acid sequence, said 5' region of said first probe hybridizes to said first region of the target nucleic acid sequence and said 3' region of said second probe hybridizes to said second region of the target nucleic acid sequence and said 5' region of said second probe hybridizes to the first probe, causing dissociation of the first and second members of the interacting label pair;

whereby generation of a detectable signal caused by dissociation of the interacting label pair indicates presence of the target nucleic acid sequence.

3. The method of claim 1 or 2, wherein said first and second regions of the target nucleic acid sequence are contiguous.

4. The method of claim 1 or 2, wherein said first and second regions of the target nucleic acid sequence are 1 nucleotide apart.

5. The method of claim 1 or 2, wherein said first and second regions of the target nucleic acid sequence are 3 or fewer nucleotides apart.

6. The method of claim 1 or 2, wherein said first and second regions of the target nucleic acid sequence are 7 or fewer nucleotides apart.

7. The method of claim 1 or 2, wherein the interacting label pair comprises donor and acceptor moieties.

8. The method of claim 1 or 2, wherein the interacting label pair comprises an enzyme.

9. The method of claim 8, wherein the interacting label pair comprises an enzyme and an inhibitor of said enzyme.

10. The method of claim 1 or 2, wherein the interacting label pair is capable of energy transfer.

11. The method of claim 1 or 2, wherein the interacting label pair comprises a fluorophore and a quencher.

12. The method of claim 1 or 2, wherein the method further comprises measuring the magnitude of the signal generated, whereby said magnitude indicates the quantity of the target nucleic acid sequence.

13. The method of claim 1, wherein the method further comprises extension of the 3' end of the second probe along a sequence in the 5' region of the first probe using a nucleotide polymerase.

14. The method of claim 1 or 2, wherein the target nucleic acid sequence is attached to an analyte.

15. The method of claim 1 or 2, wherein the target nucleic acid sequence is attached to a solid support.

16. The method of claim 1 or 2, wherein the target nucleic acid sequence comprises DNA.

17. The method of claim 1 or 2, wherein the target nucleic acid sequence comprises RNA.

18. The method of claim 1 or 2, wherein the target nucleic acid sequence comprises DNA and RNA.

19. The method of claim 1 or 2, wherein the target nucleic acid sequence comprises PNA.

20. The method of claim 1 or 2, wherein at least one of the probes comprises DNA.

21. The method of claim 1 or 2, wherein at least one of the probes comprises RNA.

22. The method of claim 1 or 2, wherein at least one of the probes comprises DNA and RNA.

23. The method of claim 1 or 2, wherein at least one of the probes comprises PNA.

24. The method of claim 1 or 2, wherein the region of the second probe which is hybridizable to a sequence of the first probe comprises a modified nucleotide that causes enhanced affinity to the sequence in the region of the first probe relative to an unmodified nucleotide.

25. The method of claim 1 or 2, wherein said detectable signal is of a greater magnitude than a detectable signal associated with the interacting label pair when the third probe is hybridized to the first probe.

26. The method of claim 1 or 2, wherein said detectable signal is of a lesser magnitude than a detectable signal associated with the interacting label pair when the third probe is hybridized to the first probe.

27. The method of claim 1 or 2, wherein the method further comprises amplifying the target nucleic acid sequence.

28. The method of claim 1 or 2, wherein the first probe or the second probe is allele-specific.

29. The method of claim 1 or 2, wherein the first probe and the second probe are allele-specific.

30. A method of determining whether a target nucleic acid sequence is present in a sample, said method comprising:

contacting said sample with a first probe, a second probe, a third probe, and a nucleotide polymerase, under conditions allowing hybridization of the first and second probes to the target nucleic acid sequence, if present, and hybridization of the first probe to the third probe, in the absence of the target nucleic acid sequence, and allowing nucleic acid polymerization, wherein:

(i) the first probe comprises (a) a polynucleotide comprising a 3' region which hybridizes to a first region of the target nucleic acid sequence, if present,
(b) a first member of an interacting label pair; and
(ii) the second probe comprises a polynucleotide comprising a 5' region which hybridizes to a second region of the target nucleic acid sequence, if present; and
(iii) the third probe comprises
(a) a polynucleotide sequence which hybridizes to a sequence in the 5' region of the first probe, and
(b) a second member of an interacting label pair;
wherein when said third probe is hybridized to said first probe, said first and second members of the interacting label pair are brought into proximity and interact;
and wherein, in the presence of the target nucleic acid sequence, said 3' region of said first probe hybridizes to said first region of the target nucleic acid sequence and said 5' region of said second probe hybridizes to said second region of the target nucleic acid sequence;
and wherein the 3' end of said second probe is extended by said nucleotide polymerase along the first probe by template switching, causing dissociation of the first and second members of the interacting label pair;
whereby generation of detectable signal caused by dissociation of the interacting label pair indicates presence of the target nucleic acid sequence.

31. A method of determining whether a target nucleic acid sequence is present in a sample, said method comprising:
contacting said sample with a first probe and a second probe, under conditions allowing hybridization of the first and second probes to the target nucleic acid sequence, if present, and hybridization of a first nucleotide sequence in the 5' region of the first probe with a second nucleotide sequence in the 5' region of the first probe, in the absence of the target nucleic acid sequence, and hybridization of at the second probe the first probe when the second probe is hybridized to the target nucleic acid sequence, wherein:
(i) the first probe comprises a polynucleotide comprising
(a) a 3' region which hybridizes to a first region of the target nucleic acid sequence, if present, and
(b) a 5' region comprising said first and second nucleotide sequences which hybridize to each other in the absence of the target nucleic acid sequence, and two members of an interacting label pair;
(ii) the second probe comprises a polynucleotide comprising
(a) a 5' region which hybridizes to a second region of the target nucleic acid sequence, if present and
(b) a 3' region which hybridizes to a sequence in the 5' region of the first probe, if the target polynucleotide is present;
wherein, when said first and second nucleotide sequences in the 5' region of the first probe hybridize, said first and second members of the interacting label pair are brought into proximity and interact; and
wherein, in the presence of the target nucleic acid sequence, said first probe and said second probe hybridize to the target nucleic acid sequence and said second probe hybridizes to the first probe, causing dissociation of the first and second members of the interacting label pair;
whereby generation of detectable signal caused by dissociation of the interacting label pair indicates presence of the target nucleic acid sequence.

32. A method of determining whether a target nucleic acid sequence is present in a sample, said method comprising:
contacting said sample with a first probe and a second probe, under conditions allowing hybridization of the first and second probes to the target nucleic acid sequence, if present, and hybridization of a first nucleotide sequence in the 3' region of the first probe with a second nucleotide sequence in the 3' region of the first probe, in the absence of the target nucleic acid sequence, and hybridization of at the second probe the first probe when the second probe is hybridized to the target nucleic acid sequence, wherein:
(i) the first probe comprises a polynucleotide comprising
(a) a 5' region which is hybridizes to a first region of the target nucleic acid sequence, if present, and
(b) a 3' region comprising said first and second nucleotide sequences which hybridize to each other in the absence of the target nucleic acid sequence, and two members of an interacting label pair;
(ii) the second probe comprises a polynucleotide comprising
(a) a 3' region which hybridizes to a second region of the target nucleic acid sequence, if present and
(b) a 5' region which hybridizes to a sequence in the 3' region of the first probe, if the target polynucleotide is present;
wherein, when said first and second nucleotide sequences in the 3' region of the first probe hybridize, said first and second members of the interacting label pair are brought into proximity and interact; and
wherein, in the presence of the target nucleic acid sequence, said first probe and said second probe hybridize to the target nucleic acid sequence and said second probe hybridizes to the first probe, causing dissociation of the first and second members of the interacting label pair;
whereby generation of detectable signal caused by dissociation of the interacting label pair indicates presence of the target nucleic acid sequence.

33. A method of determining whether a target nucleic acid sequence contains a sequence alteration relative to a reference nucleic acid sequence, said method comprising:
(a) contacting said target nucleic acid sequence with a first probe, a second probe, and a third probe, and
(b) contacting said reference nucleic acid sequence with a first probe, a second probe, and a third probe,
wherein said contact of the target nucleic acid sequence with the first, second, and third probes, and said contact of the reference nucleic acid sequence with the first, second, and third probes, occur under conditions allowing hybridization of the first and second probes to the reference nucleic acid sequence, and hybridization of the first probe to the third probe, in the absence of the reference nucleic acid sequence, and hybridization of the second probe to the first probe when the second probe is hybridized to the reference nucleic acid sequence, wherein:
(i) the first probe comprises
(a) a polynucleotide comprising a 3' region which hybridizes to a first region of the reference nucleic acid sequence, if present, and
(b) a first member of an interacting label pair;
(ii) the second probe comprises
(a) a polynucleotide comprising a 5' region which hybridizes to a second region of the reference nucleic acid sequence, if present, and (b) a 3' region which hybridizes to a sequence in the 5' region of the first probe, if the reference nucleic acid sequence is present; and (iii) the third probe comprises
(a) a polynucleotide which hybridizes to a sequence in the 5' region of the first probe, and
(b) a second member of an interacting label pair;

wherein when said third probe is hybridized to said first probe, said first and second members of the interacting label pair are brought into proximity and interact;

and wherein, in the presence of the reference nucleic acid sequence, said 3' region of said first probe hybridizes to said first region of the reference nucleic acid sequence and said 5' region of said second probe hybridizes to said second region of the reference nucleic acid sequence and said 3' region of said second probe hybridizes to the first probe, causing dissociation of the first and second members of the interacting label pair;

and comparing detectable signal generated by contacting said first, second, and third probes with the reference nucleic acid sequence with detectable signal generated by contacting said first, second, and third probes with target nucleic acid sequence;

whereby reduced signal generation by the target nucleic acid sequence as compared to the reference nucleic acid sequence indicates the presence of an altered sequence in the target nucleic acid sequence relative to the reference nucleic acid sequence.

34. A method of determining whether a target nucleic acid sequence contains a sequence alteration relative to a reference nucleic acid sequence, said method comprising:

(a) contacting said target nucleic acid sequence with a first probe, a second probe, and a third probe, and
(b) contacting said reference nucleic acid sequence with a first probe, a second probe, and a third probe, wherein said contact of the target nucleic acid sequence with the first, second, and third probes, and said contact of the reference nucleic acid sequence with the first, second, and third probes, occur under conditions allowing hybridization of the first and second probes to the reference nucleic acid sequence, and hybridization of the first probe to the third probe, in the absence of the reference nucleic acid sequence, and hybridization of the second probe to the first probe when the second probe is hybridized to the reference nucleic acid sequence, wherein:

(i) the first probe comprises
(a) a polynucleotide comprising a 5' region which hybridizes to a first region of the reference nucleic acid sequence, if present, and
(b) a first member of an interacting label pair;
(ii) the second probe comprises
(a) a polynucleotide comprising a 3' region which hybridizes to a second region of the reference nucleic acid sequence, if present, and
(b) a 5' region which hybridizes to a sequence in the 3' region of the first probe, if the reference nucleic acid sequence is present; and
(iii) the third probe comprises
(a) a polynucleotide which hybridizes to a sequence in the 5' region of the first probe, and
(b) a second member of an interacting label pair;

wherein when said third probe is hybridized to said first probe, said first and second members of the interacting label pair are brought into proximity and interact;

and wherein, in the presence of the reference nucleic acid sequence, said 5' region of said first probe hybridizes to said first region of the reference nucleic acid sequence and said 3' region of said second probe hybridizes to said second region of the reference nucleic acid sequence and said 5' region of said second probe hybridizes to the first probe, causing dissociation of the first and second members of the interacting label pair;

and comparing detectable signal generated by contacting said first, second, and third probes with the reference nucleic acid sequence with detectable signal generated by contacting said first, second, and third probes with target nucleic acid sequence;

whereby reduced signal generation by the target nucleic acid sequence as compared to the reference nucleic acid sequence indicates the presence of an altered sequence in the target nucleic acid sequence relative to the reference nucleic acid sequence.

35. A method of determining whether one or more of a plurality of target nucleic acid sequences is present in a sample, said method comprising:

contacting said sample with a plurality of probe sets, each set comprising a first probe, a second probe, and a third probe, under conditions allowing hybridization of the first and second probes to a target nucleic acid sequence, if present, and hybridization of the first probe to the third probe, in the absence of said target nucleic acid sequence, and hybridization of the second probe to the first probe when the second probe is hybridized to said target nucleic acid sequence, wherein:

(i) the first probe comprises
(a) a polynucleotide comprising a 3' region which hybridizes to a first region of said target nucleic acid sequence, if present, and
(b) a first member of an interacting label pair;
(ii) the second probe comprises
(a) a polynucleotide comprising a 5' region which hybridizes to a second region of said target nucleic acid sequence, if present, and
(b) a 3' region which hybridizes to a sequence in the 5' region of the first probe, if said target nucleic acid sequence is present;
(iii) the third probe comprises
(a) a polynucleotide which hybridizes to a sequence in the 5' region of the first probe, and
(b) a second member of an interacting label pair;

wherein when said third probe is hybridized to said first probe, said first and second members of the interacting label pair are brought into proximity and interact;

and wherein, in the presence of said target nucleic acid sequence, said 3' region of said first probe hybridizes to said first region of said target nucleic acid sequence and said 5' region of said second probe hybridizes to said second region of said target nucleic acid sequence and said 3' region of said second probe hybridizes to the first probe, causing dissociation of the first and second members of the interacting label pair;

whereby generation of a detectable signal caused by dissociation of the interacting label pair indicates presence of said target nucleic acid sequence; and wherein each probe set comprises an interacting label pair which generates a detectable signal which is different from the signals of the interacting label pairs of every other probe set, and generation of two or more signals indicates presence of a plurality of target nucleic acid sequences.

36. A method of determining whether one or more of a plurality of target nucleic acid sequences is present in a sample, said method comprising:

contacting said sample with a plurality of probe sets, each set comprising a first probe, a second probe, and a third probe, under conditions allowing hybridization of the first and second probes to a target nucleic acid sequence, if present, and hybridization of the first probe to the third probe, in the absence of said target nucleic acid sequence, and hybridization of the second probe to the first probe when the second probe is hybridized to said target nucleic acid sequence, wherein:
  (i) the first probe comprises
    (a) a polynucleotide comprising a 5' region which hybridizes to a first region of said target nucleic acid sequence, if present, and
    (b) a first member of an interacting label pair;
  (ii) the second probe comprises
    (a) a polynucleotide comprising a 3' region which hybridizes to a second region of said target nucleic acid sequence, if present, and
    (b) a 5' region which hybridizes to a sequence in the 3' region of the first probe, if said target nucleic acid sequence is present;
  (iii) the third probe comprises
    (a) a polynucleotide which hybridizes to a sequence in the 3' region of the first probe, and
    (b) a second member of an interacting label pair;
wherein when said third probe is hybridized to said first probe, said first and second members of the interacting label pair are brought into proximity and interact;
and wherein, in the presence of said target nucleic acid sequence, said 5' region of said first probe hybridizes to said first region of said target nucleic acid sequence and said 3' region of said second probe hybridizes to said second region of said target nucleic acid sequence and said 5' region of said second probe hybridizes to the first probe, causing dissociation of the first and second members of the interacting label pair;
whereby generation of a detectable signal caused by dissociation of the interacting label pair indicates presence of said target nucleic acid sequence; and
wherein each probe set comprises an interacting label pair which generates a detectable signal which is different from the signals of the interacting label pairs of every other probe set, and generation of two or more signals indicates presence of a plurality of target nucleic acid sequences.

37. A composition comprising a first probe, a second probe and a third probe, wherein:
  (i) the first probe comprises
    (a) a polynucleotide comprising a 3' region which hybridizes to a first region of a target nucleic acid sequence, if present, and
    (b) a first member of an interacting label pair;
  (ii) the second probe comprises
    (a) a polynucleotide comprising a 5' region which hybridizes to a second region of the target nucleic acid sequence, if present, and
    (b) a 3' region which hybridizes to a sequence in the 5' region of the first probe, if the target nucleic acid sequence is present;
  (iii) the third probe comprises
    (a) a polynucleotide which hybridizes to a sequence in the 5' region of the first probe, and
    (b) a second member of an interacting label pair;
wherein when said third probe is hybridized to said first probe, said first and second members of the interacting label pair are brought into proximity and interact;
and wherein, in the presence of the target nucleic acid sequence, said 3' region of said first probe hybridizes to said first region of the target nucleic acid sequence and said 5' region of said second probe hybridizes to said second region of the target nucleic acid sequence and said 3' region of said second probe hybridizes to the first probe, causing dissociation of the first and second members of the interacting label pair;
whereby generation of a detectable signal caused by dissociation of the interacting label pair indicates presence of the target nucleic acid sequence.

38. A composition comprising a first probe, a second probe and a third probe, wherein:
  (i) the first probe comprises
    (a) a polynucleotide comprising a 5' region which hybridizes to a first region of a target nucleic acid sequence, if present, and
    (b) a first member of an interacting label pair;
  (ii) the second probe comprises
    (a) a polynucleotide comprising a 3' region which hybridizes to a second region of the target nucleic acid sequence, if present, and
    (b) a 5' region which hybridizes to a sequence in the 3' region of the first probe, if the target nucleic acid sequence is present;
  (iii) the third probe comprises
    (a) a polynucleotide which hybridizes to a sequence in the 3' region of the first probe, and
    (b) a second member of an interacting label pair;
wherein when said third probe is hybridized to said first probe, said first and second members of the interacting label pair are brought into proximity and interact;
and wherein, in the presence of the target nucleic acid sequence, said 5' region of said first probe hybridizes to said first region of the target nucleic acid sequence and said 3' region of said second probe hybridizes to said second region of the target nucleic acid sequence and said 5' region of said second probe hybridizes to the first probe, causing dissociation of the first and second members of the interacting label pair;
whereby generation of a detectable signal caused by dissociation of the interacting label pair indicates presence of the target nucleic acid sequence.

39. The composition of claim 36 or 37, wherein the interacting moiety pair comprises a fluorophore and a quencher.

40. The composition of claim 36, further comprising a nucleotide polymerase.

41. The composition of claim 36 or 37, further comprising the target nucleic acid sequence.

42. The composition of claim 36 or 37, further comprising a reference nucleic acid sequence to which the target nucleic acid sequence is to be compared.

43. A kit for determining whether a target nucleic acid is present in a sample or quantifying a target nucleic acid sequence, comprising a first probe, a second probe and a third probe, wherein:
  (i) the first probe comprises
    (a) a polynucleotide comprising a 3' region which hybridizes to a first region of a target nucleic acid sequence, if present, and
    (b) a first member of an interacting label pair;
  (ii) the second probe comprises
    (a) a polynucleotide comprising a 5' region which hybridizes to a second region of the target nucleic acid sequence, if present, and (b) a 3' region which hybridizes to a sequence in the 5' region of the first probe, if the target nucleic acid sequence is present; and (iii) the third probe comprises
(a) a polynucleotide which hybridizes to a sequence in the 5' region of the first probe, and
(b) a second member of an interacting label pair;

wherein when said third probe is hybridized to said first probe, said first and second members of the interacting label pair are brought into proximity and interact;

and wherein, in the presence of the target nucleic acid sequence, said 3' region of said first probe hybridizes to said first region of the target nucleic acid sequence and said 5' region of said second probe hybridizes to said second region of the target nucleic acid sequence and said 3' region of said second probe hybridizes to the first probe, causing dissociation of the first and second members of the interacting label pair;

whereby generation of a detectable signal caused by dissociation of the interacting label pair indicates presence of the target nucleic acid sequence.

44. A kit for determining whether a target nucleic acid is present in a sample or quantifying a target nucleic acid sequence, comprising a first probe, a second probe and a third probe, wherein:

(i) the first probe comprises
(a) a polynucleotide comprising a 5' region which hybridizes to a first region of a target nucleic acid sequence, if present, and
(b) a first member of an interacting label pair;

(ii) the second probe comprises
(a) a polynucleotide comprising a 3' region which hybridizes to a second region of the target nucleic acid sequence, if present, and
(b) a 5' region which hybridizes to a sequence in the 3' region of the first probe, if the target nucleic acid sequence is present;

(iii) the third probe comprises
(a) a polynucleotide which hybridizes to a sequence in the 3' region of the first probe, and
(b) a second member of an interacting label pair;

wherein when said third probe is hybridized to said first probe, said first and second members of the interacting label pair are brought into proximity and interact;

and wherein, in the presence of the target nucleic acid sequence, said 5' region of said first probe hybridizes to said first region of the target nucleic acid sequence and said 3' region of said second probe hybridizes to said second region of the target nucleic acid sequence and said 5' region of said second probe hybridizes to the first probe, causing dissociation of the first and second members of the interacting label pair;

whereby generation of a detectable signal caused by dissociation of the interacting label pair indicates presence of the target nucleic acid sequence.

45. The kit of claim 43 or 44, further comprising a reference nucleic acid sequence to which the target nucleic acid sequence may be compared.

46. The kit of claim 43 or 44, further comprising instructions for use of the kit to determine the presence of the target nucleic acid sequence in a sample or quantify the target nucleic acid sequence.

* * * * *

UNITED STATES PATENT AND TRADEMARK OFFICE
CERTIFICATE OF CORRECTION

PATENT NO. : 6,815,164 B2
DATED : November 9, 2004
INVENTOR(S) : Nurith Kurn

It is certified that error appears in the above-identified patent and that said Letters Patent is hereby corrected as shown below:

<u>Column 45, line 46 through Column 48, line 30,</u>
Please delete claims 37-46 and insert the following --37. The method of claim 30, 31, 32, 33, 34, 35, or 36, wherein said first and second regions of the target nucleic acid sequence are contiguous.

38. The method of claim 30, 31, 32, 33, 34, 35, or 36, wherein said first and second regions of the target nucleic acid sequence are 1 nucleotide apart.

39. The method of claim 30, 31, 32, 33, 34, 35, or 36, wherein said first and second regions of the target nucleic acid sequence are 3 or fewer nucleotides apart.

40. The method of claim 30, 31, 32, 33, 34, 35, or 36, wherein said first and second regions of the target nucleic acid sequence are 7 or fewer nucleotides apart.

41. The method of claim 30, 31, 32, 33, 34, 35, or 36, wherein the interacting label pair comprises donor and acceptor moieties.

42. The method of claim 30, 31, 32, 33, 34, 35, or 36, wherein the interacting label pair comprises an enzyme.

43. The method of claim 42, wherein the interacting label pair comprises an enzyme and an inhibitor of said enzyme.

44. The method of claim 30, 31, 32, 33, 34, 35, or 36, wherein the interacting label pair is capable of energy transfer.

45. The method of claim 30, 31, 32, 33, 34, 35, or 36, wherein the interacting label pair comprises a fluorophore and a quencher.

46. The method of claim 30, 31, 32, 33, 34, 35, or 36, wherein the method further comprises measuring the magnitude of the signal generated, whereby said magnitude indicates the quantity of the target nucleic acid sequence.

47. The method of claim 30, 31, 33, or 35, wherein the method further comprises extension of the 3' end of the second probe along a sequence in the 5' region of the first probe using a nucleotide polymerase.

48. The method of claim 30, 31, 32, 33, 34, 35, or 36, wherein the target nucleic acid sequence is attached to an analyte.

49. The method of claim 30, 31, 32, 33, 34, 35, or 36, wherein the target nucleic acid sequence is attached to a solid support.

50. The method of claim 30, 31, 32, 33, 34, 35, or 36, wherein the target nucleic acid sequence comprises DNA.

51. The method of claim 30, 31, 32, 33, 34, 35, or 36, wherein the target nucleic acid sequence comprises RNA.

52. The method of claim 30, 31, 32, 33, 34, 35, or 36, wherein the target nucleic acid sequence comprises DNA and RNA.

53. The method of claim 30, 31, 32, 33, 34, 35, or 36, wherein the target nucleic acid sequence comprises PNA.

54. The method of claim 30, 31, 32, 33, 34, 35, or 36, wherein at least one of the probes comprises DNA.

UNITED STATES PATENT AND TRADEMARK OFFICE
CERTIFICATE OF CORRECTION

PATENT NO. : 6,815,164 B2
DATED : November 9, 2004
INVENTOR(S) : Nurith Kurn

It is certified that error appears in the above-identified patent and that said Letters Patent is hereby corrected as shown below:

Columns 45-48 (cont'd),

55. The method of claim 30, 31, 32, 33, 34, 35, or 36, wherein at least one of the probes comprises RNA.

56. The method of claim 30, 31, 32, 33, 34, 35, or 36, wherein at least one of the probes comprises DNA and RNA.

57. The method of claim 30, 31, 32, 33, 34, 35, or 36, wherein at least one of the probes comprises PNA.

58. The method of claim 31, 32, 33, 34, 35, or 36, wherein the region of the second probe which is hybridizable to a sequence of the first probe comprises a modified nucleotide that causes enhanced affinity to the sequence in the region of the first probe relative to an unmodified nucleotide.

59. The method of claim 30, 31, 32, 33, 34, 35, or 36, wherein said detectable signal is of a greater magnitude than a detectable signal associated with the interacting label pair when the third probe is hybridized to the first probe.

60. The method of claim 30, 31, 32, 33, 34, 35, or 36, wherein said detectable signal is of a lesser magnitude than a detectable signal associated with the interacting label pair when the third probe is hybridized to the first probe.

61. The method of claim 30, 31, 32, 33, 34, 35, or 36, wherein the method further comprises amplifying the target nucleic acid sequence.

62. The method of claim 30, 31, 32, 33, 34, 35, or 36, wherein the first probe or the second probe is allele-specific.

63. The method of claim 30, 31, 32, 33, 34, 35, or 36, wherein the first probe and the second probe are allele-specific.--

Signed and Sealed this

Fifteenth Day of February, 2005

JON W. DUDAS
*Director of the United States Patent and Trademark Office*